(12) United States Patent
Stern

(10) Patent No.: US 12,609,202 B2
(45) Date of Patent: Apr. 21, 2026

(54) METHOD AND SYSTEM FOR AUTOMATED DIFFERENTIAL MEDICAL DIAGNOSIS ASSESMENT

(71) Applicant: Experity, Inc., Machesney Park, IL (US)

(72) Inventor: David E. Stern, Rockford, IL (US)

(73) Assignee: Experity, Inc., Machesney Park, IL (US)

( * ) Notice: Subject to any disclaimer, the term of this patent is extended or adjusted under 35 U.S.C. 154(b) by 0 days.

(21) Appl. No.: 18/625,041

(22) Filed: Apr. 2, 2024

(65) Prior Publication Data

US 2024/0249845 A1     Jul. 25, 2024

(51) Int. Cl.
| | |
|---|---|
| *G16H 50/20* | (2018.01) |
| *G16H 10/60* | (2018.01) |
| *G16H 15/00* | (2018.01) |
| *G16H 50/30* | (2018.01) |
| *G16H 50/70* | (2018.01) |
| *G16H 70/20* | (2018.01) |
| *G16H 80/00* | (2018.01) |

(52) U.S. Cl.
CPC .............. *G16H 50/20* (2018.01); *G16H 10/60* (2018.01); *G16H 15/00* (2018.01); *G16H 50/30* (2018.01); *G16H 50/70* (2018.01); *G16H 70/20* (2018.01); *G16H 80/00* (2018.01)

(58) Field of Classification Search
None
See application file for complete search history.

(56) References Cited

U.S. PATENT DOCUMENTS

| | | | |
|---|---|---|---|
| 3,714,486 | A | 1/1973 | McCrary |
| 3,783,251 | A | 1/1974 | Pavkovich |
| 3,783,288 | A | 1/1974 | Barbour |
| 3,839,708 | A | 10/1974 | Bredesen |
| 3,946,236 | A | 3/1976 | Roberts |
| 4,051,522 | A | 9/1977 | Healy et al. |

(Continued)

OTHER PUBLICATIONS

Sep. 2019 and 2024, Medical Decision Making, American College of Cardiology.

(Continued)

*Primary Examiner* — Devin C Hein
(74) *Attorney, Agent, or Firm* — Lesavich High-Tech Law Group, S.C.; Stephen Lesavich

(57)     ABSTRACT

A method and system for automated differential medical diagnosis. Final diagnosis information including a final diagnosis for one or more patient complaints for a specific patient at a medical facility and differential diagnosis information including one or more likely differential diagnoses and one or more critical differential diagnoses associated with the final diagnosis for the specific patient at the medical facility, a visit summary, a medical record and a treatment plan or the specific patient at the medical facility are determined. Plural different types of complexities and plural types of risks associated with determining the final diagnosis, the one or more differential diagnoses, the one or more critical diagnosis associated with the final diagnosis, the visit summary, the medical record and the treatment plan for the one or more patient complaints for the specific patient at the medical facility are reduced.

20 Claims, 17 Drawing Sheets

(56)                    References Cited

U.S. PATENT DOCUMENTS

| | | | |
|---|---|---|---|
| 4,290,114 A | 9/1981 | Sinay |
| 4,315,309 A | 2/1982 | Coli |
| 4,408,181 A | 10/1983 | Nakayama |
| 4,489,387 A | 12/1984 | Lamb |
| 4,491,725 A | 1/1985 | Pritchard |
| 4,553,206 A | 11/1985 | Smutek |
| 4,630,274 A | 12/1986 | Schafer |
| 4,658,370 A | 4/1987 | Erman |
| 4,667,292 A | 5/1987 | Mohlenbrock |
| 4,711,996 A | 12/1987 | Drexler |
| 4,745,268 A | 5/1988 | Drexler |
| 4,803,641 A | 2/1989 | Hardy |
| 4,835,372 A | 5/1989 | Gombrich |
| 4,857,713 A | 8/1989 | Brown |
| 4,857,716 A | 8/1989 | Gombrich |
| 4,858,121 A | 8/1989 | Barber |
| 4,878,175 A | 10/1989 | Norden-Paul |
| 4,937,743 A | 6/1990 | Rassman |
| 4,987,538 A | 1/1991 | Johnson |
| 5,001,630 A | 3/1991 | Wiltfong |
| 5,002,630 A | 3/1991 | Kermani |
| 5,018,067 A | 5/1991 | Mohlenbrock |
| 5,065,315 A | 11/1991 | Garcia |
| 5,070,452 A | 12/1991 | Doyle |
| 5,072,383 A | 12/1991 | Brimm |
| 5,077,666 A | 12/1991 | Brimm |
| 5,099,424 A | 3/1992 | Schneiderman |
| 5,148,366 A | 9/1992 | Buchanan |
| 5,225,976 A | 7/1993 | Tawil |
| 5,235,507 A | 8/1993 | Sackler |
| 5,235,702 A | 8/1993 | Miller |
| 5,253,164 A | 10/1993 | Holloway |
| 5,301,105 A | 4/1994 | Cummings |
| 5,307,262 A | 4/1994 | Ertel |
| 5,319,543 A | 6/1994 | Wilhelm |
| 5,324,077 A | 6/1994 | Kessler |
| 5,325,293 A | 6/1994 | Dorne |
| 5,359,509 A | 10/1994 | Little |
| 5,365,425 A | 11/1994 | Torma |
| 5,392,209 A | 2/1995 | Eason |
| 5,404,292 A | 4/1995 | Hendrickson |
| 5,420,409 A | 5/1995 | Longacre |
| 5,465,082 A | 11/1995 | Chaco |
| 5,467,268 A | 11/1995 | Sisley |
| 5,471,382 A | 11/1995 | Tallman |
| 5,482,008 A | 1/1996 | Stafford |
| 5,483,443 A | 1/1996 | Milstein |
| 5,486,999 A | 1/1996 | Mebane |
| 5,490,196 A | 2/1996 | Rudich |
| 5,504,796 A | 4/1996 | Silveria |
| 5,510,606 A | 4/1996 | Worthington |
| 5,519,607 A | 5/1996 | Tawil |
| 5,557,514 A | 9/1996 | Seare |
| 5,583,758 A | 12/1996 | McIlroy |
| 5,583,759 A | 12/1996 | Rensimer et al. |
| 5,583,760 A | 12/1996 | Klesse |
| 5,621,779 A | 4/1997 | Hughes |
| 5,644,778 A | 7/1997 | Burks |
| 5,661,291 A | 8/1997 | Ahearn |
| 5,663,999 A | 9/1997 | Siochi |
| 5,664,109 A | 9/1997 | Johnson |
| 5,664,207 A | 9/1997 | Crumpler |
| 5,671,282 A | 9/1997 | Wolff |
| 5,672,154 A | 9/1997 | Sillen |
| 5,700,998 A | 12/1997 | Palti |
| 5,724,379 A | 3/1998 | Perkins |
| 5,754,622 A | 5/1998 | Hughes |
| 5,772,585 A | 6/1998 | Lavin |
| 5,819,228 A | 10/1998 | Spiro |
| 5,832,447 A | 11/1998 | Rieker |
| 5,835,897 A | 11/1998 | Dang |
| 5,842,976 A | 12/1998 | Williamson |
| 5,845,253 A | 12/1998 | McIlroy et al. |
| 5,845,254 A | 12/1998 | Lockwood |
| 5,845,269 A | 12/1998 | Kortge |
| 5,848,426 A | 12/1998 | Wang |
| 5,867,553 A | 2/1999 | Gordon |
| 5,915,241 A | 6/1999 | Giannini |
| 5,923,014 A | 7/1999 | Szymusiak |
| 5,924,074 A | 7/1999 | Evans |
| 5,930,759 A | 7/1999 | Moore |
| 5,953,704 A | 9/1999 | McIlroy |
| 5,970,463 A | 10/1999 | Cave |
| 5,971,279 A | 10/1999 | Raistrick |
| 5,979,757 A | 11/1999 | Tracy |
| 6,159,013 A | 12/2000 | Parienti |
| 6,192,400 B1 | 2/2001 | Hanson |
| 6,208,973 B1 | 3/2001 | Boyer |
| 6,222,452 B1 | 4/2001 | Ahlstrom |
| 6,342,839 B1 | 1/2002 | Curkendall |
| 6,347,329 B1 | 2/2002 | Evans |
| 6,366,651 B1 | 4/2002 | Griffith |
| 6,370,511 B1 | 4/2002 | Dang |
| 6,393,404 B2 | 5/2002 | Waters |
| 6,464,136 B2 | 10/2002 | Walsh |
| 6,497,358 B1 | 12/2002 | Walsh |
| 6,529,876 B1 | 3/2003 | Dart |
| 6,592,517 B2 | 7/2003 | Pratt |
| 6,597,948 B1 | 7/2003 | Rockwell |
| 6,603,464 B1 | 8/2003 | Rabin |
| 6,629,876 B1 | 10/2003 | Park et al. |
| 6,637,649 B2 | 10/2003 | Walsh |
| 6,655,583 B2 | 12/2003 | Walsh |
| 6,824,052 B2 | 11/2004 | Walsh |
| 6,830,180 B2 | 12/2004 | Walsh |
| 7,624,027 B1 | 11/2009 | Stern et al. |
| 8,341,141 B2 | 12/2012 | Krislov |
| 8,412,147 B2 | 4/2013 | Hunter |
| 8,463,765 B2 | 6/2013 | Lesavich |
| 8,533,015 B2 | 9/2013 | Meegan |
| 8,542,809 B2 | 9/2013 | Bookstaff |
| 8,589,372 B2 | 11/2013 | Krislov |
| 8,606,594 B2 | 12/2013 | Stern |
| 8,738,396 B2 | 5/2014 | Green |
| 9,037,564 B2 | 5/2015 | Lesavich et al. |
| 9,137,250 B2 | 9/2015 | Lesavich et al. |
| 9,361,479 B2 | 6/2016 | Lesavich et al. |
| 9,569,771 B2 | 2/2017 | Lesavich et al. |
| 9,842,188 B2 | 12/2017 | Stern |
| 10,249,388 B2 | 4/2019 | Zabetian |
| 10,713,243 B2 | 7/2020 | Stern |
| 10,860,171 B2* | 12/2020 | Ash ...................... G16H 10/60 |
| 11,361,853 B2 | 6/2022 | Stern |
| 11,972,865 B1* | 4/2024 | Kabir .................... G16H 15/00 |
| 12,051,506 B2* | 7/2024 | Holub ................... G16H 70/20 |
| 2002/0145634 A1 | 10/2002 | Gueramy et al. |
| 2007/0214002 A1 | 9/2007 | Smith et al. |
| 2010/0094657 A1 | 4/2010 | Stern et al. |
| 2011/0208710 A1 | 8/2011 | Lesavich |
| 2012/0278622 A1 | 11/2012 | Lesavich et al. |
| 2013/0231947 A1 | 9/2013 | Shusterman |
| 2014/0100885 A1 | 4/2014 | Stern |
| 2014/0189792 A1 | 7/2014 | Lesavich et al. |
| 2015/0379301 A1 | 12/2015 | Lesavich et al. |
| 2016/0321431 A1* | 11/2016 | Kutty ................. G06F 16/9535 |
| 2016/0321654 A1 | 11/2016 | Lesavich et al. |
| 2017/0169171 A1* | 6/2017 | Loeb ..................... G16H 20/40 |
| 2018/0114595 A1 | 4/2018 | Stern |
| 2020/0098476 A1* | 3/2020 | Loscutoff .............. G16H 50/70 |
| 2020/0342966 A1 | 10/2020 | Stern |
| 2021/0407672 A1* | 12/2021 | Zumbrun .............. G16H 20/10 |

OTHER PUBLICATIONS

Jul. 19, 2023, Misdiagnosis Seriously Harms 795,000 People Annually, Lisa O'Mary, WEBMD.

* cited by examiner

PROTOCOL STACK

Figure 7A:
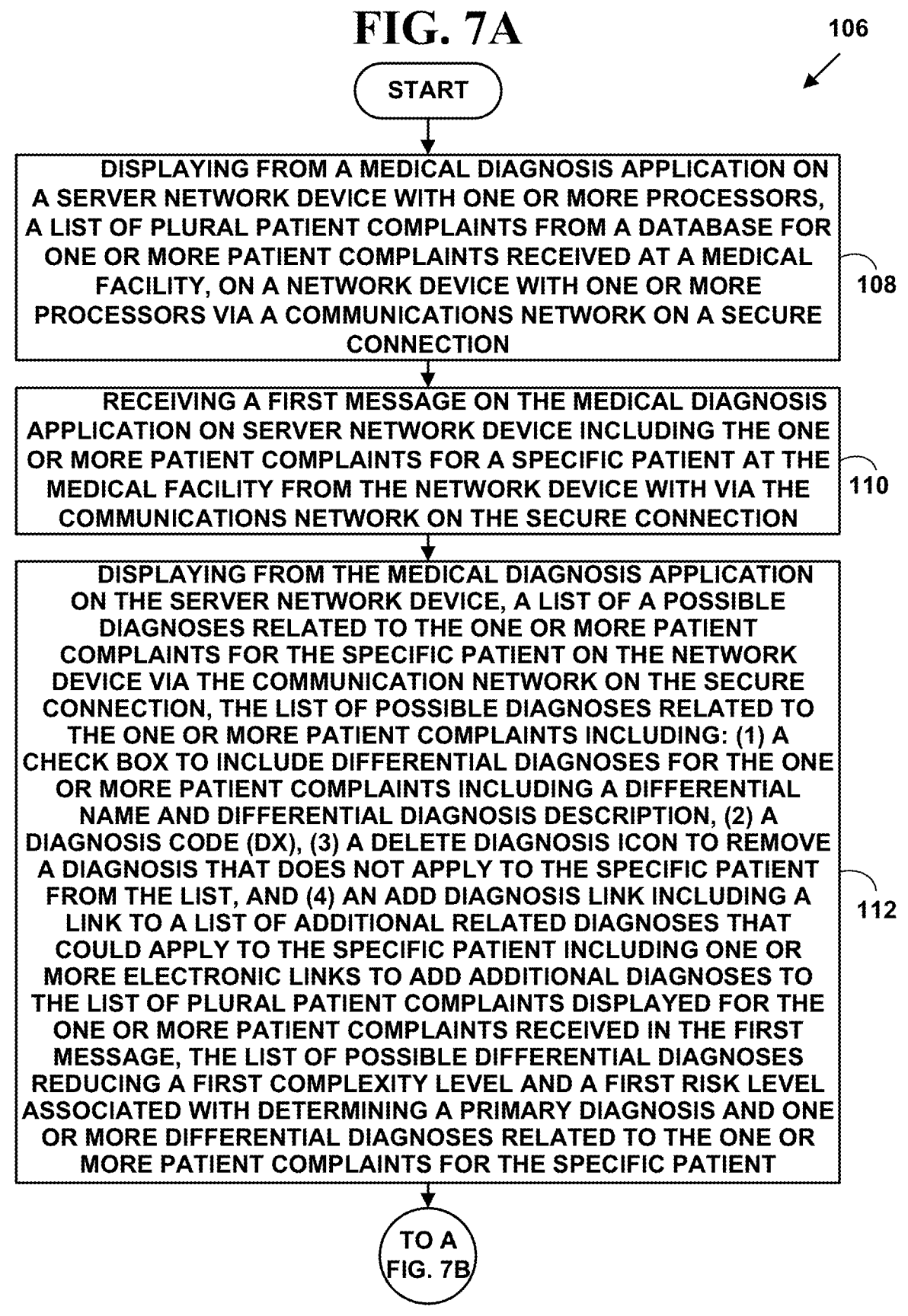

( START )

DISPLAYING FROM A MEDICAL DIAGNOSIS APPLICATION ON A SERVER NETWORK DEVICE WITH ONE OR MORE PROCESSORS, A LIST OF PLURAL PATIENT COMPLAINTS FROM A DATABASE FOR ONE OR MORE PATIENT COMPLAINTS RECEIVED AT A MEDICAL FACILITY, ON A NETWORK DEVICE WITH ONE OR MORE PROCESSORS VIA A COMMUNICATIONS NETWORK ON A SECURE CONNECTION          108

RECEIVING A FIRST MESSAGE ON THE MEDICAL DIAGNOSIS APPLICATION ON SERVER NETWORK DEVICE INCLUDING THE ONE OR MORE PATIENT COMPLAINTS FOR A SPECIFIC PATIENT AT THE MEDICAL FACILITY FROM THE NETWORK DEVICE WITH VIA THE COMMUNICATIONS NETWORK ON THE SECURE CONNECTION          110

DISPLAYING FROM THE MEDICAL DIAGNOSIS APPLICATION ON THE SERVER NETWORK DEVICE, A LIST OF A POSSIBLE DIAGNOSES RELATED TO THE ONE OR MORE PATIENT COMPLAINTS FOR THE SPECIFIC PATIENT ON THE NETWORK DEVICE VIA THE COMMUNICATION NETWORK ON THE SECURE CONNECTION, THE LIST OF POSSIBLE DIAGNOSES RELATED TO THE ONE OR MORE PATIENT COMPLAINTS INCLUDING: (1) A CHECK BOX TO INCLUDE DIFFERENTIAL DIAGNOSES FOR THE ONE OR MORE PATIENT COMPLAINTS INCLUDING A DIFFERENTIAL NAME AND DIFFERENTIAL DIAGNOSIS DESCRIPTION, (2) A DIAGNOSIS CODE (DX), (3) A DELETE DIAGNOSIS ICON TO REMOVE A DIAGNOSIS THAT DOES NOT APPLY TO THE SPECIFIC PATIENT FROM THE LIST, AND (4) AN ADD DIAGNOSIS LINK INCLUDING A LINK TO A LIST OF ADDITIONAL RELATED DIAGNOSES THAT COULD APPLY TO THE SPECIFIC PATIENT INCLUDING ONE OR MORE ELECTRONIC LINKS TO ADD ADDITIONAL DIAGNOSES TO THE LIST OF PLURAL PATIENT COMPLAINTS DISPLAYED FOR THE ONE OR MORE PATIENT COMPLAINTS RECEIVED IN THE FIRST MESSAGE, THE LIST OF POSSIBLE DIFFERENTIAL DIAGNOSES REDUCING A FIRST COMPLEXITY LEVEL AND A FIRST RISK LEVEL ASSOCIATED WITH DETERMINING A PRIMARY DIAGNOSIS AND ONE OR MORE DIFFERENTIAL DIAGNOSES RELATED TO THE ONE OR MORE PATIENT COMPLAINTS FOR THE SPECIFIC PATIENT          112

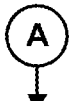

RECEIVING A SECOND MESSAGE ON THE MEDICAL DIAGNOSIS APPLICATION ON SERVER NETWORK DEVICE INCLUDING ONE OR MORE SELECTION INPUTS WITH DIAGNOSIS INFORMATION SELECTED FOR THE ONE OR MORE PATIENT COMPLAINTS FOR THE SPECIFIC PATIENT AT THE MEDICAL FACILITY FROM THE NETWORK DEVICE WITH VIA THE COMMUNICATIONS NETWORK ON THE SECURE CONNECTION          114

DISPLAYING FROM THE MEDICAL DIAGNOSIS APPLICATION ON SERVER NETWORK DEVICE, DIAGNOSIS INFORMATION AND DIFFERENTIAL DIAGNOSIS INFORMATION RELATED TO THE ONE OR MORE PATIENT COMPLAINTS FOR THE SPECIFIC PATIENT ON THE NETWORK DEVICE VIA THE COMMUNICATION NETWORK ON THE SECURE CONNECTION; THE DIAGNOSIS AND DIFFERENTIAL DIAGNOSIS INFORMATION INCLUDING: (1) A DETERMINED DIAGNOSIS SECTION INCLUDING A GRAPHICAL CHECKBOX TO ADD THE DETERMINED DIAGNOSIS AS A FINAL DIAGNOSIS FOR THE ONE OR MORE PATIENT COMPLAINTS FOR THE SPECIFIC PATIENT AT THE MEDICAL FACILITY, (2) A DIFFERENTIAL DIAGNOSIS SECTION INCLUDING A GRAPHICAL CHECKBOX TO ADD ONE OR MORE DIFFERENTIAL DIAGNOSES FOR THE SPECIFIC PATIENT AT THE MEDICAL FACILITY, (3) A DIAGNOSIS NAME INCLUDING A DIAGNOSIS DESCRIPTION AND AN INTERNATIONAL CLASSIFICATION OF DISEASES (ICD) DIAGNOSTIC CODE, (4) A LIST OF EVALUATION METHODS USED TO INCLUDE AND RULE OUT ONE OR MORE DIFFERENTIAL DIAGNOSES AND SELECT A FINAL DIAGNOSIS, (5) A DIAGNOSIS (DX) MORBIDITY THREAT INCLUDING A MORBIDITY THREAT LEVEL FOR THE DIAGNOSIS, AND (6) A GRAPHICAL SEARCH ELECTRONIC LINK TO SEARCH FOR ADDITIONAL DIAGNOSES TO ADD TO THE LIKELY DIFFERENTIAL DIAGNOSIS LIST;          116

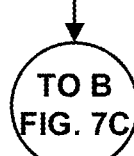

RECEIVING A THIRD MESSAGE ON THE MEDICAL DIAGNOSIS APPLICATION ON SERVER NETWORK DEVICE INCLUDING ONE OR MORE SELECTION INPUTS WITH DIFFERENTIAL DIAGNOSIS INFORMATION SELECTED FOR THE PATIENT COMPLAINT FOR THE SPECIFIC PATIENT AT THE MEDICAL FACILITY FROM THE NETWORK DEVICE WITH VIA THE COMMUNICATIONS NETWORK ON THE SECURE CONNECTION          118

DETERMING ON THE MEDICAL DIAGNOSIS APPLICATION ON SERVER NETWORK DEVICE WITH ONE OR MORE DIAGNOSIS METHODS WITH INFORMATION FROM THE FIRST MESSAGE, SECOND MESSAGE AND THIRD MESSAGES: (1) FINAL DIAGNOSIS INFORMATION INCLUDING A FINAL DIAGNOSIS FOR THE ONE OR MORE PATIENT COMPLAINTS FOR THE SPECIFIC PATIENT AT THE MEDICAL FACILITY, AND (2) DIFFERENTIAL DIAGNOSIS INFORMATION INCLUDING ONE OR MORE LIKELY DIFFERENTIAL DIAGNOSES AND ONE OR MORE CRITICAL DIFFERENTIAL DIAGNOSES FOR THE SPECIFIC PATIENT AT THE MEDICAL FACILITY          120

CREATING ON THE MEDICAL DIAGNOSIS APPLICATION ON SERVER NETWORK DEVICE WITH THE ONE OR MORE DIAGNOSIS METHODS WITH INFORMATION FROM THE FIRST MESSAGE, SECOND MESSAGE AND THIRD MESSAGES: (1) AN ELECTRONIC VISIT SUMMARY FOR THE SPECIFIC PATIENT AT THE MEDICAL FACILITY SUPPLIED TO THE SPECIFIC PATENT AT THE MEDICAL FACILITY INCLUDING THE DETERMINED FINAL DIAGNOSIS INFORMATION AND THE DETERMINED DIFFERENTIAL DIAGNOSIS INFORMATION, (2) A NEW MEDICAL RECORD FOR THE SPECIFIC PATIENT AT THE MEDICAL FACILITY INCLUDING THE DETERMINED FINAL DIAGNOSIS INFORMATION AND DIFFERENTIAL DIAGNOSIS INFORMATION, AND (3) A TREATMENT PLAN FOR THE SPECIFIC PATENT AT THE MEDICAL FACILITY INCLUDING THE DETERMINED FINAL DIAGNOSIS INFORMATION AND DIFFERENTIAL DIAGNOSIS INFORMATION,THE CREATED ELECTRONIC VISIT SUMMARY, THE CREATED NEW MEDICAL RECORD AND THE CREATED TREATMENT PLAN REDUCING A SECOND COMPLEXITY LEVEL AND A SECOND RISK LEVEL ASSOCIATED WITH DETERMINING A FINAL DIAGNOSIS, ONE OR MORE DIFFERENTIAL DIAGNOSES CREATED FOR THE ONE OR MORE PATIENT COMPLAINTS FOR THE SPECIFIC PATIENT AT THE MEDICAL FACILITY          122

STORING FROM THE MEDICAL DIAGNOSIS APPLICATION ON SERVER NETWORK DEVICE THE DETERMINED FINAL DIAGNOSIS INFORMATION AND DIFFERENTIAL DIAGNOSIS INFORMATION, THE CREATED ELECTRONIC VISIT SUMMARY, NEW MEDICAL RECORD AND THE TREATMENT PLAN FOR THE SPECIFIC PATENT AT THE MEDICAL FACILITY IN THE DATABASE — 124

DISPLAYING FROM THE MEDICAL DIAGNOSIS APPLICATION ON SERVER NETWORK DEVICE, DIAGNOSIS SUMMARY INFORMATION RELATED TO THE ONE ON MORE PATIENT COMPLAINTS FOR THE SPECIFIC PATIENT AT MEDICAL FACILITY ON THE NETWORK DEVICE VIA THE COMMUNICATION NETWORK ON THE SECURE CONNECTION. THE DIAGNOSIS SUMMARY INFORMATION INCLUDING: FINAL DIAGNOSIS INFORMATION INCLUDING: (1) THE FINAL DIAGNOSIS FOR THE ONE OR MORE PATIENT COMPLAINTS FOR THE SPECIFIC PATIENT AT THE MEDICAL FACILITY, (2) THE DIFFERENTIAL DIAGNOSIS INFORMATION INCLUDING ONE OR MORE LIKELY DIFFERENTIAL DIAGNOSES AND CRITICAL DIFFERENTIAL DIAGNOSES FOR THE SPECIFIC PATIENT AT THE MEDICAL FACILITY, (3) THE CREATED ELECTRONIC VISIT SUMMARY FOR THE SPECIFIC PATIENT AT THE MEDICAL FACILITY SUPPLIED TO THE SPECIFIC PATENT AT THE MEDICAL FACILITY, (4)THE CREATED NEW MEDICAL RECORD FOR THE SPECIFIC PATIENT AT THE MEDICAL FACILITY AND (5) THE CREATED TREATMENT PLAN FOR THE SPECIFIC PATIENT SUPPLIED TO THE SPECIFIC PATENT AT THE MEDICAL FACILITY — 126

SENDING A FOURTH MESSAGE FROM THE MEDICAL DIAGNOSIS APPLICATION ON SERVER NETWORK DEVICE TO THE SERVER NETWORK DEVICE VIA THE COMMUNICATION NETWORK ON THE SECURE CONNECTION, THE FOURTH MESSAGE INCLUDING THE CREATED NEW MEDICAL RECORD, THE CREATED ELECTRONIC VISIT SUMMARY AND THE CREATED TREATMENT PLAN FOR THE SPECIFIC PATIENT AT THE MEDICAL FACILITY — 128

END

Figure 13:
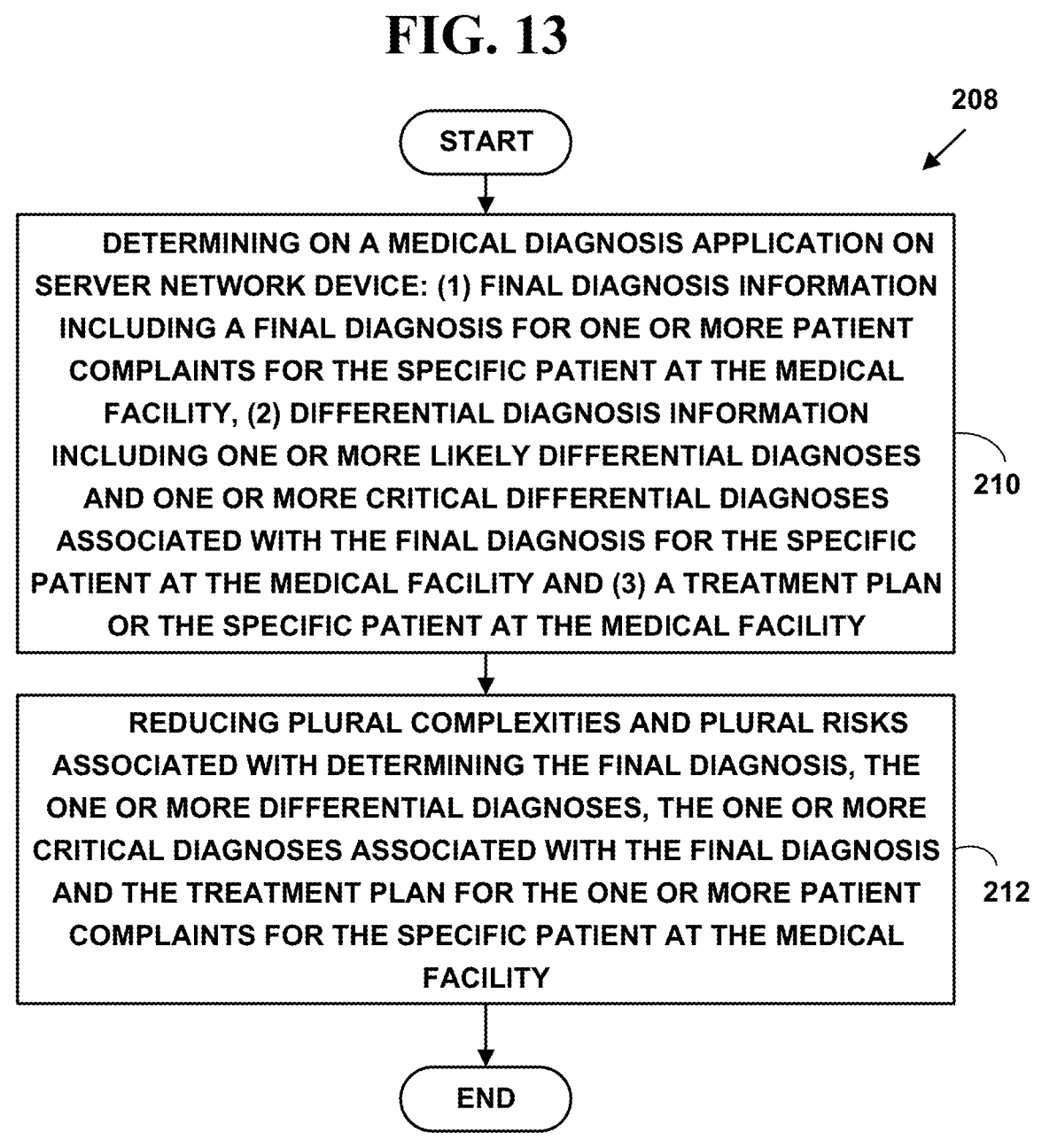

START

DETERMINING ON A MEDICAL DIAGNOSIS APPLICATION ON SERVER NETWORK DEVICE: (1) FINAL DIAGNOSIS INFORMATION INCLUDING A FINAL DIAGNOSIS FOR ONE OR MORE PATIENT COMPLAINTS FOR THE SPECIFIC PATIENT AT THE MEDICAL FACILITY, (2) DIFFERENTIAL DIAGNOSIS INFORMATION INCLUDING ONE OR MORE LIKELY DIFFERENTIAL DIAGNOSES AND ONE OR MORE CRITICAL DIFFERENTIAL DIAGNOSES ASSOCIATED WITH THE FINAL DIAGNOSIS FOR THE SPECIFIC PATIENT AT THE MEDICAL FACILITY AND (3) A TREATMENT PLAN OR THE SPECIFIC PATIENT AT THE MEDICAL FACILITY

210

REDUCING PLURAL COMPLEXITIES AND PLURAL RISKS ASSOCIATED WITH DETERMINING THE FINAL DIAGNOSIS, THE ONE OR MORE DIFFERENTIAL DIAGNOSES, THE ONE OR MORE CRITICAL DIAGNOSES ASSOCIATED WITH THE FINAL DIAGNOSIS AND THE TREATMENT PLAN FOR THE ONE OR MORE PATIENT COMPLAINTS FOR THE SPECIFIC PATIENT AT THE MEDICAL FACILITY

212

END

FIG. 14

START

DETERMINING ON A MEDICAL DIAGNOSIS APPLICATION ON SERVER NETWORK DEVICE DIFFERENTIAL DIAGNOSIS INFORMATION INCLUDING ONE OR MORE LIKELY DIFFERENTIAL DIAGNOSES AND ONE OR MORE CRITICAL DIFFERENTIAL DIAGNOSES ASSOCIATED INCLUDING DETERMINING PLURAL MORBIDITY THREAT LEVELS FOR THE ONE OR MORE LIKELY DIFFERENTIAL DIAGNOSES AND THE ONE OR MORE CRITICAL DIFFERENTIAL DIAGNOSES FOR THE SPECIFIC PATIENT AT THE MEDICAL FACILITY

216

REDUCING PLURAL COMPLEXITIES AND PLURAL RISKS ASSOCIATED WITH THE DETERMINED ONE OR MORE DIFFERENTIAL DIAGNOSES AND THE DETERMINED ONE OR MORE CRITICAL DIAGNOSES FOR THE SPECIFIC PATIENT AT THE MEDICAL FACILITY WITH THE DETERMINED PLURAL MORBIDITY THREAT LEVELS FOR THE SPECIFIC PATIENT AT THE MEDICAL FACILITY

218

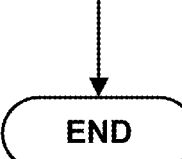

END

METHOD AND SYSTEM FOR AUTOMATED DIFFERENTIAL MEDICAL DIAGNOSIS ASSESMENT

CROSS REFERENCES TO RELATED APPLICATIONS

Not Applicable.

COPYRIGHT NOTICE

FIELD OF INVENTION

This invention relates to medical diagnosis. More specifically, it relates to a method and system for providing automated differential medical diagnosis assessment.

BACKGROUND OF THE INVENTION

There are many different types of medical information that are routinely collected when a patient has an emergency or non-emergency medical problem, or visit a provider for a routine visit or annual physical. The medical information includes such information as a patient history including current symptoms the patient is feeling, any medication the patient is currently taking, any past medical problems or surgeries the patient has, known allergies, other family history, prescribed medications, etc. The patient history is used to determine a final diagnosis and one or more differential diagnoses for one or more patient complaints.

In medicine, a "differential diagnosis" is a method of analysis that distinguishes a particular disease or condition from others that present with similar clinical features.

Determining a final diagnosis and one or more differential diagnoses from a patient encounter is complex and presents many risks, even for an experienced medical doctor. There is a significant risk of complications, morbidity, mortality, associated with the patient's complaints due to misdiagnoses of medical problems associated with the patient complaints. A patient risk diagnosis is based on the patient's current health status, past health history, and other risk factors that may increase the patient's likelihood of experiencing a health problem.

Patient morbidity is defined as a patient having a disease or a symptom of a disease. Patient mortality is defined as a death rate, or a number of deaths in a certain group of people in a certain period of time.

According the American College of Cardiology, a number of possible diagnoses and differential diagnoses that must be considered is based on a number and types of patient complaints addressed during a patient encounter significantly increases a complexity of establishing a correct medical diagnosis, and treatment plan decisions that are made by the medical doctor.

According to WEBMD, an estimated 795,000 people in the U.S. die or are permanently disabled each year due to misdiagnoses of medical problems. Strokes top the list of misdiagnosed medical problems that cause serious harm in a patient. On average, medical researchers estimate that 11% of patient complaints result in a misdiagnosis, although the error rate varies widely depending on a disease. It has been estimated that reducing diagnostic errors by 50% for stroke, sepsis, other infections, pneumonia, pulmonary embolism and lung cancer could cut permanent disabilities and deaths by 150,000 per year.

There have been a number of automated solutions to evaluate patient complaints in medical facilities and determine medical diagnoses.

For example, U.S. Pat. No. 7,624,027, that issued to Stern, et. al. teaches "a method and system for automated medical records processing. The method and system includes plural paper and electronic templates specifically designed such that they reduce the complexity of collecting patient encounter information and help generate the appropriate number and type medical codes for a specific type of medical practice when processed. The method and system also includes processing applications that allow easy and automated collection, processing, displaying and recording of medical codes (e.g., diagnosis codes, billing codes, insurance codes, etc.). The medical codes and other types of processed patient encounter information are displayed in real-time on electronic templates immediately after a patient encounter."

U.S. Pat. No. 8,606,594, that issued to Stern, et al. teaches "A method and system for automated medical records processing. The method and system includes plural electronic medical templates specifically designed such that they reduce the complexity and risk associated with collecting patient encounter information, creating a medical diagnosis and help generate the appropriate number and type medical codes for a specific type of medical practice when processed. The medical codes and other types of processed patient encounter information are displayed in real-time on electronic medical records and invoices immediately after a patient encounter."

U.S. Pat. No. 9,842,188, that issued to Stern teaches "A method and system for automated medical records processing with cloud computing. The method and system includes plural electronic medical templates specifically designed such that they reduce the complexity and risk associated with collecting patient encounter information, creating a medical diagnosis and help generate the appropriate number and type medical codes for a specific type of medical practice when processed. The medical codes and other types of processed patient encounter information are displayed in real-time on electronic medical records and invoices immediately after a patient encounter via a cloud computing network."

U.S. Pat. No. 10,714,213, that issued to Stern, teaches "A method and system for automated medical records processing with cloud computing including patient tracking for actual and virtual encounters. The method and system includes plural electronic medical templates specifically designed such that they reduce the complexity and risk associated with collecting patient encounter information, creating a medical diagnosis, tracking the patient through the medical processes at the medical facility and generate the appropriate number and type medical codes for a specific type of medical practice when processed. The medical codes and other types of processed actual or virtual patient encounter information are displayed in real-time on electronic medical records and invoices immediately after an actual or virtual patient encounter via a cloud computing network.

U.S. Pat. No. 11,861,353, that issued to Stern, teaches "A method and system for automated medical records processing with telemedicine is presented. The method and system includes plural electronic medical templates specifically designed such that they reduce the complexity and risk associated with collecting virtual patient encounter information, creating a medical diagnosis, tracking the patient through the medical processes during a telemedicine session and generate the appropriate number and type medical codes for a specific type of medical practice when processed. The medical codes and other types of processed virtual patient encounter information are displayed in real-time on electronic medical records and invoices immediately after a virtual patient encounter from a telemedicine visit.

However, none of these solutions solve all of the problems associated with differential medical diagnosis assessment. Thus, it is desirable to solve some of problems associated with automated differential medical diagnosis assessment.

SUMMARY OF THE INVENTION

In accordance with preferred embodiments of the present invention, some of the problems associated with automated differential medical diagnosis are overcome. A method and system for automated differential medical diagnosis assessment is presented.

Final diagnosis information including a final diagnosis for one or more patient complaints for a specific patient at a medical facility and plural differential diagnosis information including one or more likely differential diagnoses and one or more critical differential diagnoses associated with the final diagnosis for the specific patient at the medical facility, a visit summary, a medical record and a treatment plan or the specific patient at the medical facility are automatically determined. Plural different types of complexities and plural types of risks associated with determining the final diagnosis, the one or more differential diagnoses, the one or more critical diagnosis associated with the final diagnosis, the visit summary, the medical record and the treatment plan for the one or more patient complaints for the specific patient at the medical facility are reduced.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIGS. 7A, 7B, 7C and 7D are a flow diagram illustrating a method for providing automated differential medical diagnosis assessment;

FIG. 13 is a flow diagram illustrating a method for providing automated differential medical diagnosis assessment; and FIG. 14 is a flow diagram illustrating a method for providing automated differential medical diagnosis assessment.

DETAILED DESCRIPTION OF THE INVENTION

Figure 1:
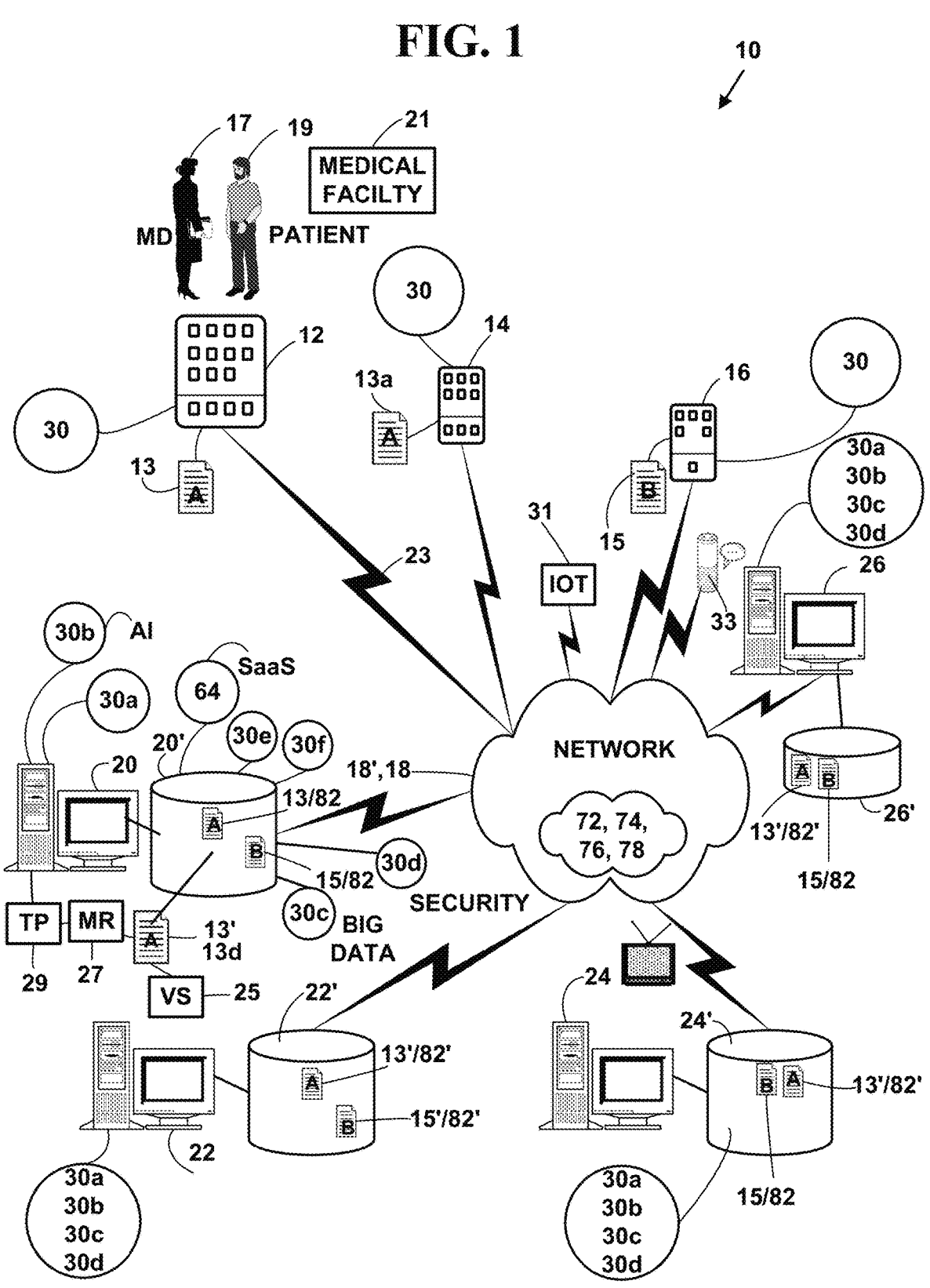
FIG. 1 is a block diagram illustrating an exemplary electronic automated differential medical diagnosis assessment processing and display system.

Exemplary Electronic Automated Differential Medical Diagnosis Assessment Processing and Display System FIG. 1 is a block diagram illustrating an exemplary electronic automated differential medical diagnosis assessment processing and display system 10. The exemplary electronic system 10 includes, but is not limited to, one or more target network devices 12, 14, 16, etc. each with one or more processors and each with a non-transitory computer readable medium.

The one or more target network devices 12, 14, 16, 31, 33 and/or wearable network devices 98-104 (FIG. 6), are used by a medical doctor 17 and/or other medical professional (e.g., nurse, nurse practitioner, physician assistant, etc.) to collect medical information including one or more complaints 13 for a specific patent 19 at a medical facility 21.

In one embodiment, the specific patient 19 is physically located at the medical facility 21 with the medical doctor 17 (or other medical personnel, etc.). In another embodiment, the specific patient 19 is not physically located at the medical facility 21, but is in contact with the medical doctor 17 (or other medical personnel, etc.) who are at the medical facility 21 via the communications network 18, 18' (e.g., via telephone, video conference, email, text, etc.). In another embodiment, the medical doctor 17 (or other medical personnel, etc.) is remote to the medical facility 21 and the specific patient 19 is physically located the medical facility 21. In other embodiment, both the medical doctor 17 (or other medical personnel, etc.) are both remote to the medical facility 21 (e.g., telemedicine, etc.). However, the present is not limited to such embodiments and other embodiments may be used to practice the invention.

The one or more target network devices 12, 14, 16 (illustrated in FIG. 1 only as a tablet and two smart phones for simplicity) also include, but are not limited to, desktop and laptop computers, tablet computers, smart phones, Internet phones, Internet appliances, personal digital/data assistants (PDA), cable television (CATV), satellite television (SATV) and Internet television set-top boxes, digital televisions including high definition television (HDTV), three-dimensional (3DTV) televisions, Internet of Things (IOT)

devices, 31, smart speakers 33, wearable network devices 98-104 (FIG. 6) and/or other types of target network devices. However, more, fewer and/or types of target network devices can be use to practice the invention.

A "smart phone" is a mobile phone 14 that offers more advanced computing ability and connectivity than a contemporary basic feature phone. Smart phones and feature phones may be thought of as handheld computers integrated with a mobile telephone, but while most feature phones are able to run applications based on platforms such as JAVA ME, a smart phone usually allows the user to install and run more advanced applications. Smart phones and/or tablet computers run complete operating system software providing a platform for application developers.

The tablet computers 12, 12' include, but are not limited to, tablet computers such as the IPAD, by APPLE, Inc., the HP Tablet, by HEWLETT PACKARD, Inc., the PLAYBOOK, by RIM, Inc., the TABLET, by SONY, Inc., etc.

The IoT network devices 31, include but are not limited to, internet network devices with a display screen, security cameras, doorbells with real-time video cameras, baby monitors, televisions, set-top boxes, lighting, heating (e.g., smart thermostats, etc.), ventilation, air conditioning (HVAC) systems, and appliances such as washers, dryers, robotic vacuums, air purifiers, ovens, refrigerators, freezers, toys, game platform controllers, game platform attachments (e.g., guns, googles, sports equipment, etc.), and/or other IoT network devices.

A "smart speaker" 33 is a type of wireless speaker and voice command device with an integrated virtual assistant that offers interactive actions and hands-free activation with the help of one "hot word" (or several "hot words"). Some smart speakers can also act as a smart device that utilizes Wi-Fi, BLUETOOTH and other wireless protocol standards to extend usage beyond audio playback, such as to control home automation devices. This can include, but is not limited to, features such as compatibility across a number of services and platforms, peer-to-peer connection through mesh networking, virtual assistants, and others. Each can have its own designated interface and features in-house, usually launched or controlled via application or home automation software. Some smart speakers also include a screen to show the user a visual response.

The target network devices 12, 14, 16, 31, 33, 98-104 are in communications with a cloud communications network 18 or a non-cloud computing network 18' via one or more wired and/or wireless communications interfaces. The cloud communications network 18, is also called a "cloud computing network" herein and the terms may be used interchangeably.

The plural target network devices 12, 14, 16, 31, 33 98-104 make requests 13, 13a 15 for electronic messages (e.g., SMS, MMS, RCS, email, etc.) via the cloud communications network 18 or non-cloud communications network 18'

The cloud communications network 18 and non-cloud communications network 18' includes, but is not limited to, communications over a wire connected to the target network devices, wireless communications, and other types of communications using one or more communications and/or networking protocols.

Plural server network devices 20, 22, 24, 26 (only four of which are illustrated for simplicity) each with one or more processors and a non-transitory computer readable medium include one or more associated databases 20', 22', 24', 26'. The plural network devices 20, 22, 24, 26 are in communications with the one or more target devices 12, 14, 16, 31,

33, 98-104 via the cloud communications network 18 and non-cloud communications network 18'.

Plural server network devices 20, 22, 24, 26 (only four of which are illustrated for simplicity) are physically located on one more public networks 76 (See FIG. 4), private networks 72, community networks 74 and/or hybrid networks 78 comprising the cloud network 18.

One or more server network devices (e.g., 20, 22, 24, 26, etc.) store portions of the electronic content 13, 13a, 15 (e.g., SMS, MMS, RCS messages, etc.) as cloud storage objects 82 (FIG. 5) as is described herein.

The plural server network devices 20, 22, 24 26, may be connected to, but are not limited to, World Wide Web servers, Internet servers, search engine servers, vertical search engine servers, social networking site servers, file servers, other types of electronic information servers, and other types of server network devices (e.g., edge servers, firewalls, routers, gateways, etc.).

The plural server network devices 20, 22, 24, 26 also include, but are not limited to, network servers used for cloud computing 18 providers, etc.

The cloud communications network 18 and non-cloud communications network 18' includes, but is not limited to, a wired and/or wireless communications network comprising one or more portions of: the Internet, an intranet, a Local Area Network (LAN), a wireless LAN (WiLAN), a Wide Area Network (WAN), a Metropolitan Area Network (MAN), a Public Switched Telephone Network (PSTN), a Wireless Personal Area Network (WPAN) and other types of wired and/or wireless communications networks 18.

The cloud communications network 18 and non-cloud communications network 18' includes one or more gateways, routers, bridges and/or switches. A gateway connects computer networks using different network protocols and/or operating at different transmission capacities. A router receives transmitted messages and forwards them to their correct destinations over the most efficient available route. A bridge is a device that connects networks using the same communications protocols so that information can be passed from one network device to another. A switch is a device that filters and forwards packets between network segments based on some pre-determined sequence (e.g., timing, sequence number, etc.).

An operating environment for the network devices of the exemplary electronic information display system 10 include a processing system with one or more high speed Central Processing Unit(s) (CPU), processors, non-transitory computer readable mediums, and/or one or other types of memories. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU-executed," or "processor-executed."

It will be appreciated that acts and symbolically represented operations or instructions include the manipulation of electrical information by the CPU or processor. An electrical system represents data bits which cause a resulting transformation or reduction of the electrical information, biological information, quantum information and the maintenance of data bits at memory locations in a memory system to thereby reconfigure or otherwise alter the CPU's or processor's operation, as well as other processing of information. The memory locations where data bits are maintained are physical locations that have particular electrical, magnetic, optical, organic quantum properties corresponding to the data bits.

The data bits may also be maintained on a non-transitory computer readable medium including magnetic disks, optical disks, organic memory, quantum memory and any other volatile (e.g., Random Access Memory (RAM)) or non-volatile (e.g., Read-Only Memory (ROM), flash memory, etc.) mass storage system readable by the CPU. The non-transitory computer readable medium includes cooperating or interconnected computer readable medium, which exist exclusively on the processing system or can be distributed among multiple interconnected processing systems that may be local or remote to the processing system.

Exemplary Electronic Content Display System

Figure 2:
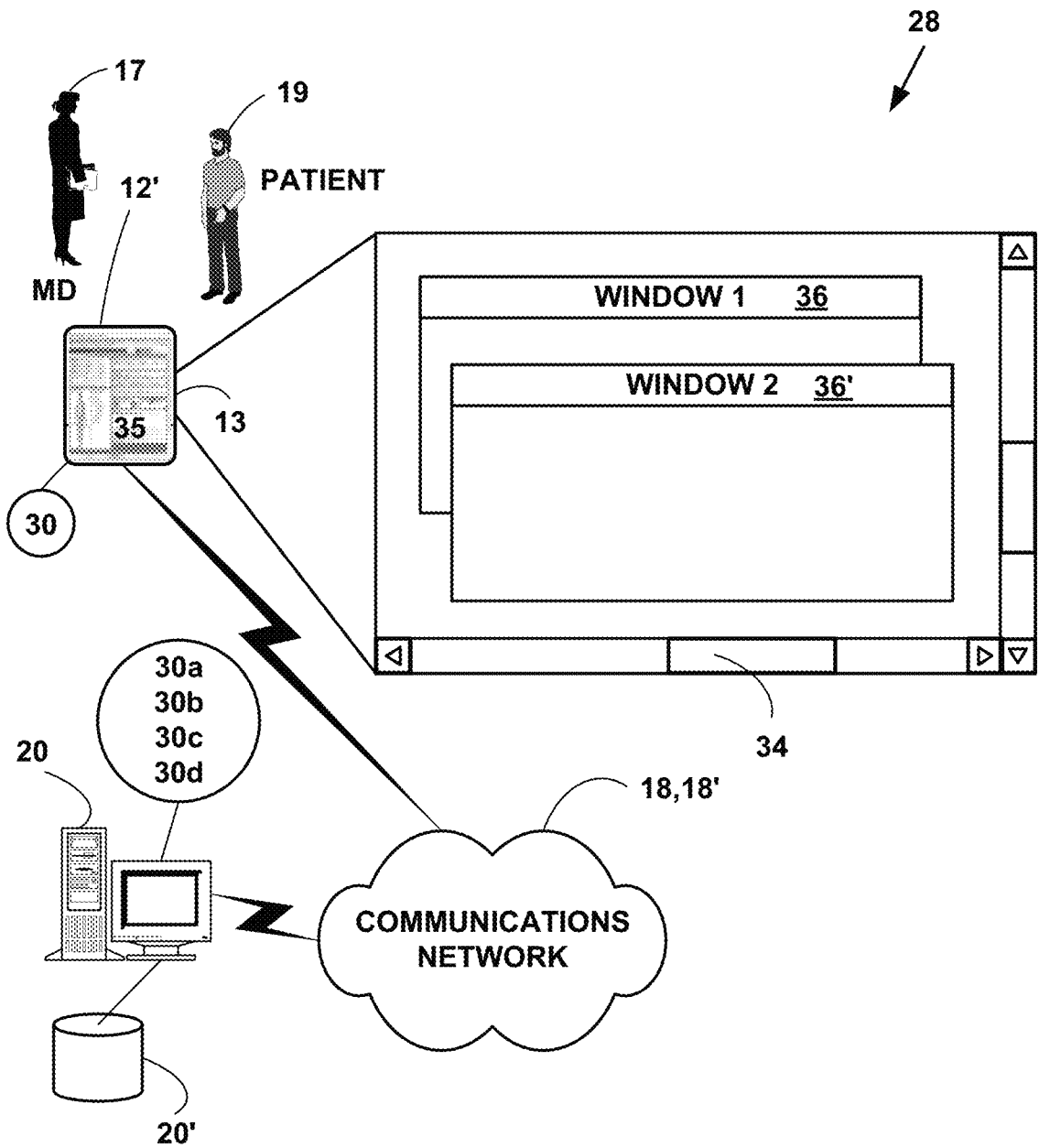
FIG. 2 is a block diagram illustrating an exemplary electronic automated differential medical diagnosis assessment display system.

FIG. 2 is a block diagram illustrating an exemplary electronic automated differential medical diagnosis assessment display system 28. The exemplary electronic message information display system 12' includes, but is not limited to a target network device (e.g., 12, etc.) with an application 30 and a display component 32. The applications 30, 30a presents a graphical user interface (GUI) 34 on the display 32 component. The GUI 32 presents a multi-window 36, 36', etc. (only two of which are illustrated) interface to a user (e.g., medical doctor 17, etc.). FIG. 2 illustrates a graphical electronic patient intake form 35. In one embodiment, patient intake form 35, includes those provided by U.S. Pat. No. 9,142,988, that issued to Stern. However, the present invention is not limited to such an embodiment and other embodiments can be used to practice the invention.

In one embodiment of the invention, the application 30, 30a is a software application. However, the present invention is not limited to this embodiment and the application 30, 30a can be hardware, firmware, hardware and/or any combination thereof. In one embodiment, the application 30, 30a includes a mobile application for a smart phone, electronic tablet and/or other network device. In one embodiment, the application 30, 30a includes web-browser based application. In one embodiment, the application 30, 30a includes a web-chat client application. In another embodiment, the application 30a, 30b, 30c, 30d, 30e, 30f includes a cloud application used on a cloud communications network 18 as a Software as a Service (SaaS). However, the present invention is not limited these embodiments and other embodiments can be used to practice the invention In another embodiment, a portion of the application 30 is executing on the target network devices 12, 14, 16, 31, 33, 98-104 and another portion of the application 30a, 30b, 30c, 30d, 30e, 30f is executing on the server network devices 20, 22, 24, 26. The applications also include one or more library applications (e.g., Application Programming Interface (API), etc.) However, the present invention is not limited these embodiments and other embodiments can be used to practice the invention.

Exemplary Networking Protocol Stack

Figure 3:
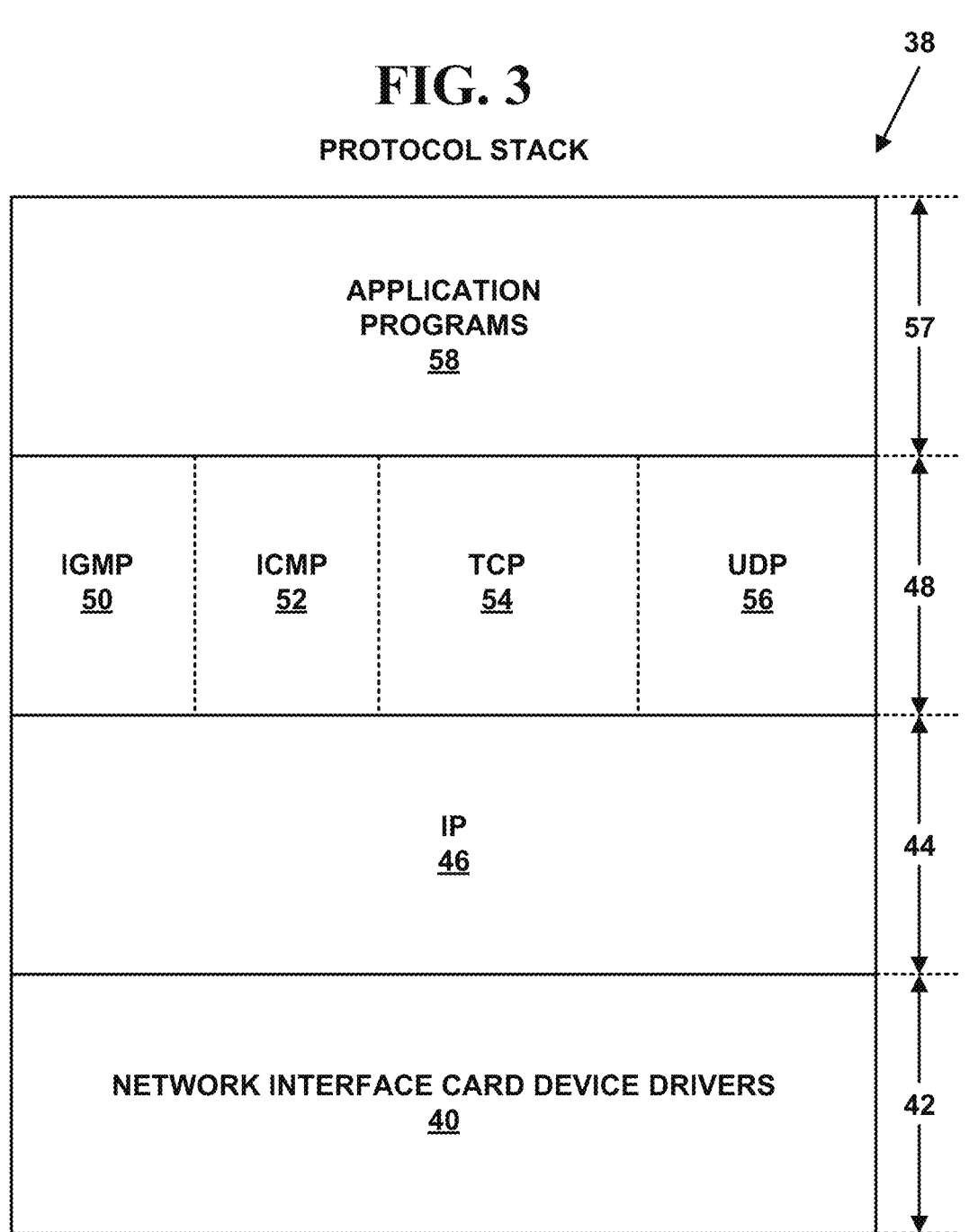
FIG. 3 is a block diagram illustrating an exemplary networking protocol stack.

FIG. 3 a block diagram illustrating a layered protocol stack 38 for network devices in the electronic message information display system 10. The layered protocol stack 38 is described with respect to Internet Protocol (IP) suites comprising in general from lowest-to-highest, a link 42, network 44, transport 48 and application 56 layers. However, more or fewer layers could also be used, and different layer designations could also be used for the layers in the protocol stack 38 (e.g., layering based on the Open Systems Interconnection (OSI) model including from lowest-to-highest, a physical, data-link, network, transport, session, presentation and application layer.).

The network devices 12, 14, 16, 20, 22, 24, 26, 31, 98-104 are connected to the communication network 18 with Network Interface Card (NIC) cards including device drivers 40 in a link layer 42 for the actual hardware connecting the network devices 12, 14, 16, 20, 22, 24, 26, 31, 98-104 to the cloud communications network 18. For example, the NIC device drivers 40 may include a serial port device driver, a digital subscriber line (DSL) device driver, an Ethernet device driver, a wireless device driver, a wired device driver, etc. The device driver interface with the actual hardware being used to connect the network devices to the cloud communications network 18. The NIC cards have a medium access control (MAC) address that is unique to each NIC and unique across the whole cloud network 18. The Medium Access Control (MAC) protocol is used to provide a data link layer of an Ethernet LAN system and for other network systems.

Above the link layer 42 is a network layer 44 (also called the Internet Layer for Internet Protocol (IP) suites). The network layer 44 includes, but is not limited to, an IP layer 46.

IP 46 is an addressing protocol designed to route traffic within a network or between networks. However, more, fewer or other protocols can also be used in the network layer 44, and the present invention is not limited to IP 46. For more information on IP 46 see IETF RFC-791, incorporated herein by reference.

Above network layer 44 is a transport layer 48. The transport layer 48 includes, but is not limited to, an optional Internet Group Management Protocol (IGMP) layer 50, a Internet Control Message Protocol (ICMP) layer 52, a Transmission Control Protocol (TCP) layer 52 and a User Datagram Protocol (UDP) layer 54. However, more, fewer or other protocols could also be used in the transport layer 48.

Optional IGMP layer 50, hereinafter IGMP 50, is responsible for multicasting. For more information on IGMP 50 see RFC-1112, incorporated herein by reference. ICMP layer 52, hereinafter ICMP 52 is used for IP 46 control. The main functions of ICMP 52 include error reporting, reachability testing (e.g., pinging, etc.), route-change notification, performance, subnet addressing and other maintenance. For more information on ICMP 52 see RFC-792, incorporated herein by reference. Both IGMP 50 and ICMP 52 are not required in the protocol stack 38. ICMP 52 can be used alone without optional IGMP layer 50.

TCP layer 54, hereinafter TCP 54, provides a connection-oriented, end-to-end reliable protocol designed to fit into a layered hierarchy of protocols which support multi-network applications. TCP 54 provides for reliable inter-process communication between pairs of processes in network devices attached to distinct but interconnected networks. For more information on TCP 54 see RFC-793, incorporated herein by reference.

UDP layer 56, hereinafter UDP 56, provides a connectionless mode of communications with datagrams in an interconnected set of computer networks. UDP 56 provides a transaction-oriented datagram protocol, where delivery and duplicate packet protection are not guaranteed. For more information on UDP 56 see RFC-768, incorporated herein by reference. Both TCP 54 and UDP 56 are not required in protocol stack 38. Either TCP 54 or UDP 56 can be used without the other.

Above transport layer 48 is an application layer 57 where application programs 58 (e.g., 30, 30a, 30b, 30c, 30d, 30e, 30f, etc.) to carry out desired functionality for a network device reside. For example, the application programs 58 for the client network devices 12, 14, 16, 27, 31, 33, 98-104 may include web-browsers or other application programs, application program 30, while application programs for the server network devices 20, 22, 24, 26 may include other application programs (e.g., 30*a*, 30*b*, 30*c*, 30*d*, 30*e*, 30*f*, etc.).

In one embodiment, application program 30 includes an automated differential medical diagnosis assessment display system message application 30 on the target network devices 12, 14, 16, 31, 33, 106-112, and/or a medical diagnosis assessment display system message application 30*a*, an Artificial Intelligence (AI) application 30*b*, Big Data application 30*c*, Security application 30*d* and/or other applications 30*e*, 30*f*, executing on the server network devices 20, 22, 24, 26. However, the present invention is not limited to such an embodiment and more, fewer and/or other types applications can be used to practice the invention.

However, the protocol stack 38 is not limited to the protocol layers illustrated and more, fewer or other layers and protocols can also be used in protocol stack 38. In addition, other protocols from the Internet Protocol suites (e.g., Simple Mail Transfer Protocol, (SMTP), Hyper Text Transfer Protocol (HTTP), File Transfer Protocol (FTP), Dynamic Host Configuration Protocol (DHCP), DNS, etc.), Short Message Peer-to-Peer (SMPP), and/or other protocols from other protocol suites may also be used in protocol stack 38.

In addition, markup languages such as HyperText Markup Language (HTML), Extensible Markup Language (XML) and others are used.

HyperText Markup Language (HTML) is a markup language for creating web pages and other information that can be displayed in a web browser.

HTML is written in the form of HTML elements consisting of tags enclosed in angle brackets within the web page content. HTML tags most commonly come in pairs although some tags represent empty elements and so are unpaired. The first tag in a pair is the start tag, and the second tag is the end tag (they are also called opening tags and closing tags). In between these tags web designers can add text, further tags, comments and other types of text-based content.

The purpose of a web browser is to read HTML documents and compose them into visible or audible web pages. The browser does not display the HTML tags, but uses the tags to interpret the content of the page.

HTML elements form the building blocks of all websites. HTML allows images and objects to be embedded and can be used to create interactive forms. It provides a means to create structured documents by denoting structural semantics for text such as headings, paragraphs, lists, links, quotes and other items. It can embed scripts written in languages such as JavaScript which affect the behavior of HTML web pages.

Extensible Markup Language (XML) is another markup language that defines a set of rules for encoding documents in a format that is both human-readable and machine-readable. It is defined in the XML 1.0 Specification produced by the W3C, the contents of which are incorporated by reference and several other related specifications, all free open standards.

XML a textual data format with strong support via Unicode for the languages of the world. Although the design of XML focuses on documents, it is widely used for the representation of arbitrary data structures, for example in web services. The oldest schema language for XML is the Document Type Definition (DTD). DTDs within XML documents define entities, which are arbitrary fragments of text and/or markup tags that the XML processor inserts in the DTD itself and in the XML document wherever they are referenced, like character escapes.

The Short Message Peer-to-Peer (SMPP) protocol in the telecommunications industry is an open, industry standard protocol designed to provide a flexible data communication interface for the transfer of short message data between External Short Messaging Entities, Routing Entities (ESME) and Short Message Service Center (SMSC).

Preferred embodiments of the present invention include network devices and wired and wireless interfaces that are compliant with all or part of standards proposed by the Institute of Electrical and Electronic Engineers (IEEE), International Telecommunications Union-Telecommunication Standardization Sector (ITU), European Telecommunications Standards Institute (ETSI), Internet Engineering Task Force (IETF), U.S. National Institute of Security Technology (NIST), American National Standard Institute (ANSI), Wireless Application Protocol (WAP) Forum, Bluetooth Forum, or the ADSL Forum.

Wireless Interfaces

In one embodiment of the present invention, the wireless interfaces on network devices 12, 14, 16, 20, 22, 24, 26, 31, 98-104 include but are not limited to, IEEE 802.11a, 802.11b, 802.11g, 802.11n, 802.15.4 (ZigBee), "Wireless Fidelity" (Wi-Fi), "Worldwide Interoperability for Microwave Access" (WiMAX), ETSI High Performance Radio Metropolitan Area Network (HIPERMAN) or "RF Home" wireless interfaces. In another embodiment of the present invention, the wireless sensor device may include an integral or separate Bluetooth and/or infra data association (IrDA) module for wireless BLUETOOTH or wireless infrared communications. However, the present invention is not limited to such an embodiment and other 802.11xx and other types of wireless interfaces can also be used.

802.11b is a short-range wireless network standard. The IEEE 802.11b standard defines wireless interfaces that provide up to 11 Mbps wireless data transmission to and from wireless devices over short ranges. 802.11a is an extension of the 802.11b and can deliver speeds up to 54 Mbps. 802.11g deliver speeds on par with 802.11a. However, other 802.11XX interfaces can also be used and the present invention is not limited to the 802.11 protocols defined. The IEEE 802.11a, 802.11b and 802.11g standards are incorporated herein by reference.

Wi-Fi is a type of 802.11xx interface, whether 802.11b, 802.11a, dual-band, etc. Wi-Fi devices include an RF interfaces such as 2.4 GHz for 802.11b or 802.11g and 5 GHz for 802.11a.

802.15.4 (Zigbee) is low data rate network standard used for mesh network devices such as sensors, interactive toys, smart badges, remote controls, and home automation. The 802.15.4 standard provides data rates of 250 kbps, 40 kbps, and 20 kbps., two addressing modes; 16-bit short and 64-bit IEEE addressing, support for critical latency devices, such as joysticks, Carrier Sense Multiple Access/Collision Avoidance, (CSMA-CA) channel access, automatic network establishment by a coordinator, a full handshake protocol for transfer reliability, power management to ensure low power consumption for multi-month to multi-year battery usage and up to 16 channels in the 2.4 GHz Industrial, Scientific and Medical (ISM) band (Worldwide), 10 channels in the 915 MHz (US) and one channel in the 868 MHz band (Europe). The IEEE 802.15.4-2003 standard is incorporated herein by reference.

WiMAX is an industry trade organization formed by leading communications component and equipment companies to promote and certify compatibility and interoperability of broadband wireless access equipment that conforms to the IEEE 802.16XX and ETSI HIPERMAN. HIPERMAN is the European standard for metropolitan area networks (MAN).

The IEEE The 802.16a and 802.16g standards are wireless MAN technology standard that provides a wireless alternative to cable, DSL and T1/E1 for last mile broadband access. It is also used as complimentary technology to connect IEEE 802.11XX hot spots to the Internet.

The IEEE 802.16a standard for 2-11 GHz is a wireless MAN technology that provides broadband wireless connectivity to fixed, portable and nomadic devices. It provides up to 50-kilometers of service area range, allows users to get broadband connectivity without needing direct line of sight with the base station, and provides total data rates of up to 280 Mbps per base station, which is enough bandwidth to simultaneously support hundreds of businesses with T1/E1-type connectivity and thousands of homes with DSL-type connectivity with a single base station. The IEEE 802.16g provides up to 100 Mbps.

The IEEE 802.16e standard is an extension to the approved IEEE 802.16/16a/16g standard. The purpose of 802.16e is to add limited mobility to the current standard which is designed for fixed operation.

The ESTI HIPERMAN standard is an interoperable broadband fixed wireless access standard for systems operating at radio frequencies between 2 GHz and 11 GHz.

The IEEE 802.16a, 802.16e and 802.16g standards are incorporated herein by reference. WiMAX can be used to provide a WLP.

The ETSI HIPERMAN standards TR 101 031, TR 101 475, TR 101 493-1 through TR 101 493-3, TR 101 761-1 through TR 101 761-4, TR 101 762, TR 101 763-1 through TR 101 763-3 and TR 101 957 are incorporated herein by reference. ETSI HIPERMAN can be used to provide a WLP.

In one embodiment, the plural server network devices 20, 22, 24, 26 include a connection to plural network interface cards (NICs) in a backplane connected to a communications bus. The NIC cards provide gigabit/second ($1 \times 10^9$ bits/second) or greater communications speed of electronic information. This allows "scaling out" for fast electronic content retrieval. The NICs are connected to the plural server network devices 20, 22, 24, 26 and the cloud communications network 18. However, the present invention is not limited to the NICs described and other types of NICs in other configurations and connections with and/or without buses can also be used to practice the invention.

In one embodiment, of the invention, the wireless interfaces also include wireless personal area network (WPAN) interfaces. As is known in the art, a WPAN is a personal area network for interconnecting devices centered around an individual person's devices in which the connections are wireless. A WPAN interconnects all the ordinary computing and communicating devices that a person has on their desk (e.g. computer, etc.) or carry with them (e.g., PDA, mobile phone, smart phone, table computer two-way pager, etc.)

A key concept in WPAN technology is known as "plugging in." In the ideal scenario, when any two WPAN-equipped devices come into close proximity (within several meters and/or feet of each other) or within a few miles and/or kilometers of a central server (not illustrated), they can communicate via wireless communications as if connected by a cable. WPAN devices can also lock out other devices selectively, preventing needless interference or unauthorized access to secure information. Zigbee is one wireless protocol used on WPAN networks such as cloud communications network 18 or non-cloud communications network 18'.

The one or more target network devices 12, 14, 16, 20, 22, 24, 26, 31, 98-104 and one or more server network devices 20, 22, 24, 26 communicate with each other and other network devices with near field communications (NFC) and/or machine-to-machine (M2M) communications.

"Near field communication (NFC)" is a set of standards for smartphones and similar network devices to establish radio communication with each other by touching them together or bringing them into close proximity, usually no more than a few centimeters. Present applications include contactless transactions, data exchange, and simplified setup of more complex communications such as Wi-Fi. Communication is also possible between an NFC device and an unpowered NFC chip, called a "tag" including radio frequency identifier (RFID) tags 99 and/or sensor.

NFC standards cover communications protocols and data exchange formats, and are based on existing radio-frequency identification (RFID) standards including ISO/IEC 14443 and FeliCa. These standards include ISO/IEC 1809 and those defined by the NFC Forum, all of which are incorporated by reference.

An "RFID tag" is an object that can be applied to or incorporated into a product, animal, or person for the purpose of identification and/or tracking using RF signals.

An "RFID sensor" is a device that measures a physical quantity and converts it into an RF signal which can be read by an observer or by an instrument (e.g., target network devices 12, 14, 16, 20, 22, 24, 26, 31, 98-104, server network devices 20, 22, 24, 26, etc.)

"Machine to machine (M2M)" refers to technologies that allow both wireless and wired systems to communicate with other devices of the same ability. M2M uses a device to capture an event (such as option purchase, etc.), which is relayed through a network (wireless, wired cloud, etc.) to an application (software program), that translates the captured event into meaningful information. Such communication was originally accomplished by having a remote network of machines relay information back to a central hub for analysis, which would then be rerouted into a system like a personal computer.

However, modern M2M communication has expanded beyond a one-to-one connection and changed into a system of networks that transmits data many-to-one and many-to-many to plural different types of devices and appliances. The expansion of IP networks across the world has made it far easier for M2M communication to take place and has lessened the amount of power and time necessary for information to be communicated between machines.

However, the present invention is not limited to such wireless interfaces and wireless networks and more, fewer and/or other wireless interfaces can be used to practice the invention.

Wired Interfaces

In I one embodiment of the present invention, the wired interfaces include wired interfaces and corresponding networking protocols for wired connections to the Public Switched Telephone Network (PSTN) and/or a cable television network (CATV) and/or satellite television networks (SATV) and/or three-dimensional television (3DTV), including HDTV that connect the network devices 12, 14, 16, 20, 22, 24, 26, 31, 33, 98-104 via one or more twisted pairs of copper wires, digital subscriber lines (e.g. DSL, ADSL, VDSL, etc.) coaxial cable, fiber optic cable, other connection media or other connection interfaces. The PSTN is any public switched telephone network provided by AT&T, GTE, SPRINT, MCI, SBC, VERIZON and others. The CATV is any cable television network provided by the COMCAST, TIME WARNER, etc. However, the present invention is not limited to such wired interfaces and more, fewer and/or other wired interfaces can be used to practice the invention.

Television Services

In one embodiment, the cloud applications 30, 30*a*, 30*b*, 30*c*, 30*d*, 30*e*, 30*f* provide cloud SaaS 64 services and/or non-cloud application services from television services over the cloud communications network 18 or application services over the non-cloud communications network 18'. The television services include digital television services, including, but not limited to, cable television, satellite television, high-definition television, three-dimensional, televisions and other types of network devices.

However, the present invention is not limited to such television services and more, fewer and/or other television services can be used to practice the invention.

Internet Television Services

In one embodiment, the cloud applications 30, 30*a*, 30*b*, 30*c*, 30*d*, 30*e*, 30*f* provide cloud SaaS 64 services and/or non-cloud application services from Internet television services over the cloud communications network 18 or non-cloud communications network 18' The television services include Internet television, Web-TV, and/or Internet Protocol Television (IPtv) and/or other broadcast television services.

"Internet television" allows users to choose a program or the television show they want to watch from an archive of programs or from a channel directory. The two forms of viewing Internet television are streaming content directly to a media player or simply downloading a program to a viewer's set-top box, game console, computer, or other network device.

"Web-TV" delivers digital content via broadband and mobile networks. The digital content is streamed to a viewer's set-top box, game console, computer, or other network device.

"Internet Protocol television (IPtv)" is a system through which Internet television services are delivered using the architecture and networking methods of the Internet Protocol Suite over a packet-switched network infrastructure, e.g., the Internet and broadband Internet access networks, instead of being delivered through traditional radio frequency broadcast, satellite signal, and cable television formats.

However, the present invention is not limited to such Internet Television services and more, fewer and/or other Internet Television services can be used to practice the invention.

General Search Engine Services

In one embodiment, the cloud applications 30, 30*a*, 30*b*, 30*c*, 30*d*, 30*e*, 30*f* provide cloud SaaS 64 services and/or non-cloud application services from general search engine services. A search engine is designed to search for information on a cloud communications network 18 or non-cloud communications network 18' such as the Internet including World Wide Web servers, HTTP, FTP servers etc. The search results are generally presented in a list of electronic results. The information may consist of web pages, images, electronic information, multimedia information, and other types of files. Some search engines also mine data available in databases or open directories. Unlike web directories, which are maintained by human editors, search engines typically operate algorithmically and/or are a mixture of algorithmic and human input.

In one embodiment, the cloud applications 30, 30*a*, 30*b*, 30*c*, 30*d*, 30*e*, 30*f* provide cloud SaaS 64 services and/or non-cloud application services from general search engine services. In another embodiment, the cloud applications 30, 30*a*, 30*b*, 30*c*, 30*d*, 30*e*, 30*f* provide general search engine services by interacting with one or more other public search engines (e.g., GOOGLE, BING, YAHOO, etc.) and/or private search engine services.

In another embodiment, the cloud applications 30, 30*a*, 30*b*, 30*c*, 30*d*, 30*e*, 30*f* provide cloud SaaS 64 services and/or non-cloud application services from specialized search engine services, such as vertical search engine services by interacting with one or more other public vertical search engines, and/or private search engine services.

However, the present invention is not limited to such general and/or vertical search engine services and more, fewer and/or other general search engine services can be used to practice the invention.

Social Networking Services

In one embodiment, the cloud applications 30, 30*a*, 30*b*, 30*c*, 30*d*, 30*e*, 30*f* provide cloud SaaS 64 services and/or non-cloud application services from one more social networking services including to/from one or more social networking web-sites (e.g., FACEBOOK, YOUTUBE, TWITTER, INSTAGRAM, etc.). The social networking web-sites also include, but are not limited to, social couponing sites, dating web-sites, blogs, RSS feeds, and other types of information web-sites in which messages can be left or posted for a variety of social activities.

However, the present invention is not limited to the social networking services described and other public and private social networking services can also be used to practice the invention.

Security and Encryption

Network devices 12, 14, 16, 20, 22, 24, 26, 31, 33, 98-104 with wired and/or wireless interfaces of the present invention include one or more of the security and encryptions techniques via Security application 30*e*, discussed herein for secure communications on the cloud communications network 18 or non-cloud communications network 18'.

Secure connections 23 on used the on the communications network 18, 18' for communications to and/or from network devices 12, 14, 16, 20, 22, 24, 26, 31, 33, 98-104 with wired and/or wireless interfaces, and/or secure storage in databases 20', 22', 24', 26' and/or secure storage in cloud databases and cloud storage objects 82, to comply with Health Insurance Portability and Accountability Act (HIPAA) rules and protect the privacy of patent information sent over the communications network 18, 18'.

Health Insurance Portability and Accountability Act (HIPAA) is a U.S. federal law passed in 1996 that sets a national standard to protect medical records and other personal health information. The rule defines "protected health information" as health information that: (1) Identifies an individual patient, and (2) is maintained or exchanged electronically and/or in hard copy. If the i medical records and other personal health information has any components that could be used to identify a person, it is protected by HIPAA. The protection would stay with the information as long as the information is in the hands of a covered entity (e.g., a medical facility, doctors office, etc.) and/or a business associate (e.g., insurance company, billing company, etc.). The protections apply to individually identifiable information in any form, electronic or non-electronic. The paper progeny of electronic information is covered (i.e., the information would not lose its protections simply because it is printed out of a computer), and oral communications are also covered.

Application programs 58 (FIG. 2) include security and/or encryption application programs 30e integral to and/or separate from the applications 30, 30a, 30b, 30c, 30d. Security and/or encryption programs and/or applications 30e may also exist in hardware components on the network devices (12, 14, 16, 20, 22, 24, 26, 31, 98-104) described herein and/or exist in a combination of hardware, software and/or firmware.

Wireless Encryption Protocol (WEP) (also called "Wired Equivalent Privacy) is a security protocol for WiLANs defined in the IEEE 802.11b standard. WEP is cryptographic privacy algorithm, based on the Rivest Cipher 4 (RC4) encryption engine, used to provide confidentiality for 802.11b wireless data.

RC4 is cipher designed by RSA Data Security, Inc. of Bedford, Massachusetts, which can accept encryption keys of arbitrary length, and is essentially a pseudo random number generator with an output of the generator being XORed with a data stream to produce encrypted data.

One problem with WEP is that it is used at the two lowest layers of the OSI model, the physical layer and the data link layer, therefore, it does not offer end-to-end security. One another problem with WEP is that its encryption keys are static rather than dynamic. To update WEP encryption keys, an individual has to manually update a WEP key. WEP also typically uses 40-bit static keys for encryption and thus provides "weak encryption," making a WEP device a target of hackers.

The IEEE 802.11 Working Group has a security upgrade for the 802.11 standard called "802.11i." This supplemental draft standard is intended to improve WiLAN security. It describes the encrypted transmission of data between systems 802.11X WiLANs. It also defines new encryption key protocols including the Temporal Key Integrity Protocol (TKIP). The IEEE 802.11i draft standard, version 4, completed Jun. 6, 2003, is incorporated herein by reference.

The 802.11i standard is based on 802.1x port-based authentication for user and device authentication. The 802.11i standard includes two main developments: Wi-Fi Protected Access (WPA) and Robust Security Network (RSN).

WPA uses the same RC4 underlying encryption algorithm as WEP. However, WPA uses TKIP to improve security of keys used with WEP. WPA keys are derived and rotated more often than WEP keys and thus provide additional security. WPA also adds a message-integrity-check function to prevent packet forgeries.

RSN uses dynamic negotiation of authentication and selectable encryption algorithms between wireless access points and wireless devices. The authentication schemes proposed in the draft standard include Extensible Authentication Protocol (EAP). One proposed encryption algorithm is an Advanced Encryption Standard (AES) encryption algorithm.

Dynamic negotiation of authentication and encryption algorithms lets RSN evolve with the state of the art in security, adding algorithms to address new threats and continuing to provide the security necessary to protect information that WiLANs carry.

The NIST developed a new encryption standard, the Advanced Encryption Standard (AES) to keep government information secure. AES is intended to be a stronger, more efficient successor to Triple Data Encryption Standard (3DES).

DES is a popular symmetric-key encryption method developed in 1975 and standardized by ANSI in 1981 as ANSI X.3.92, the contents of which are incorporated herein by reference. As is known in the art, 3DES is the encrypt-decrypt-encrypt (EDE) mode of the DES cipher algorithm. 3DES is defined in the ANSI standard, ANSI X9.52-1998, the contents of which are incorporated herein by reference. DES modes of operation are used in conjunction with the NIST Federal Information Processing Standard (FIPS) for data encryption (FIPS 46-3, October 1999), the contents of which are incorporated herein by reference.

The NIST approved a FIPS for the AES, FIPS-197. This standard specified "Rijndael" encryption as a FIPS-approved symmetric encryption algorithm that may be used by U.S. Government organizations (and others) to protect sensitive information. The NIST FIPS-197 standard (AES FIPS PUB 197, November 2001) is incorporated herein by reference.

The NIST approved a FIPS for U.S. Federal Government requirements for information technology products for sensitive but unclassified (SBU) communications. The NIST FIPS Security Requirements for Cryptographic Modules (FIPS PUB 140-2, May 2001) is incorporated herein by reference.

RSA is a public key encryption system which can be used both for encrypting messages and making digital signatures. The letters RSA stand for the names of the inventors: Rivest, Shamir and Adleman. For more information on RSA, see U.S. Pat. No. 4,405,829, now expired and incorporated herein by reference.

"Hashing" is the transformation of a string of characters into a usually shorter fixed-length value or key that represents the original string. Hashing is used to index and retrieve items in a database because it is faster to find the item using the shorter hashed key than to find it using the original value. It is also used in many encryption algorithms.

Secure Hash Algorithm (SHA), is used for computing a secure condensed representation of a data message or a data file. When a message of any length $<2^{64}$ bits is input, the SHA-1 produces a 160-bit output called a "message digest." The message digest can then be input to other security techniques such as encryption, a Digital Signature Algorithm (DSA) and others which generates or verifies a security mechanism for the message. SHA-512 outputs a 512-bit message digest. The Secure Hash Standard, FIPS PUB 180-1, Apr. 17, 1995, is incorporated herein by reference.

Message Digest-5 (MD-5) takes as input a message of arbitrary length and produces as output a 128-bit "message digest" of the input. The MD5 algorithm is intended for digital signature applications, where a large file must be "compressed" in a secure manner before being encrypted with a private (secret) key under a public-key cryptosystem such as RSA. The IETF RFC-1321, entitled "The MD5 Message-Digest Algorithm" is incorporated here by reference.

Providing a way to check the integrity of information transmitted over or stored in an unreliable medium such as a wireless network is a prime necessity in the world of open computing and communications. Mechanisms that provide such integrity check based on a secret key are called "message authentication codes" (MAC). Typically, message authentication codes are used between two parties that share a secret key in order to validate information transmitted between these parties.

Keyed Hashing for Message Authentication Codes (HMAC), is a mechanism for message authentication using cryptographic hash functions. HMAC is used with any iterative cryptographic hash function, e.g., MD5, SHA-1, SHA-512, etc. in combination with a secret shared key. The cryptographic strength of HMAC depends on the properties of the underlying hash function. The IETF RFC-2101, entitled "HMAC: Keyed-Hashing for Message Authentication" is incorporated here by reference.

An Electronic Code Book (ECB) is a mode of operation for a "block cipher," with the characteristic that each possible block of plaintext has a defined corresponding cipher text value and vice versa. In other words, the same plaintext value will always result in the same cipher text value. Electronic Code Book is used when a volume of plaintext is separated into several blocks of data, each of which is then encrypted independently of other blocks. The Electronic Code Book has the ability to support a separate encryption key for each block type.

Diffie and Hellman (DH) describe several different group methods for two parties to agree upon a shared secret in such a way that the secret will be unavailable to eavesdroppers. This secret is then converted into various types of cryptographic keys. A large number of the variants of the DH method exist including ANSI X9.42. The IETF RFC-2631, entitled "Diffie-Hellman Key Agreement Method" is incorporated here by reference.

The HyperText Transport Protocol (HTTP) Secure (HTTPs), is a standard for encrypted communications on the World Wide Web. HTTPs is actually just HTTP over a Secure Sockets Layer (SSL). For more information on HTTP, see IETF RFC-2616 incorporated herein by reference.

The SSL protocol is a protocol layer which may be placed between a reliable connection-oriented network layer protocol (e.g. TCP/IP) and the application protocol layer (e.g. HTTP). SSL provides for secure communication between a source and destination by allowing mutual authentication, the use of digital signatures for integrity, and encryption for privacy.

The SSL protocol is designed to support a range of choices for specific security methods used for cryptography, message digests, and digital signatures. The security methods are negotiated between the source and destination at the start of establishing a protocol session. The SSL 2.0 protocol specification, by Kipp E. B. Hickman, 1995 is incorporated herein by reference. More information on SSL is available at the domain name See "netscape.com/eng/security/SSL_2.html."

Transport Layer Security (TLS) provides communications privacy over the Internet. The protocol allows client/server applications to communicate over a transport layer (e.g., TCP) in a way that is designed to prevent eavesdropping, tampering, or message forgery. For more information on TLS see IETF RFC-2246, incorporated herein by reference.

In one embodiment, the security functionality includes Cisco Compatible EXtensions (CCX). CCX includes security specifications for makers of 802.11xx wireless LAN chips for ensuring compliance with Cisco's proprietary wireless security LAN protocols. As is known in the art, Cisco Systems, Inc. of San Jose, California is supplier of networking hardware and software, including router and security products.

However, the present invention is not limited to such security and encryption methods described herein and more, fewer and/or other types of security and encryption methods can be used to practice the invention. The security and encryption methods described herein can also be used in various combinations and/or in different layers of the protocol stack 38 with each other.

Cloud Computing Networks

Figure 4:
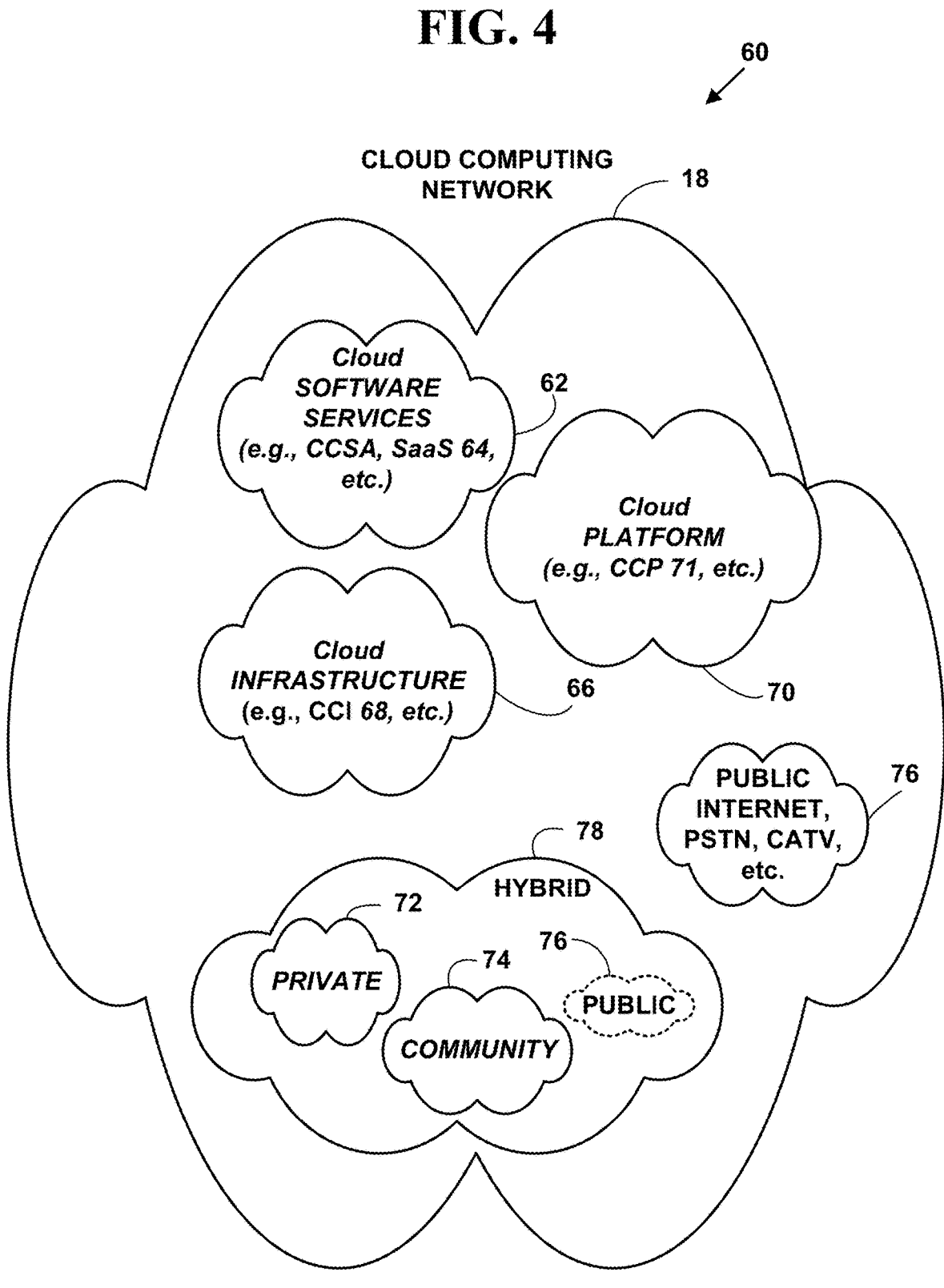
FIG. 4 is a block diagram illustrating an exemplary cloud communications network.

FIG. 4 is a block diagram 60 illustrating an exemplary cloud computing network 18. The cloud computing network 18 is also referred to as a "cloud communications network" 18. However, the present invention is not limited to this cloud computing model and other cloud computing models can also be used to practice the invention. The exemplary cloud communications network includes both wired and/or wireless components of public and private networks.

In one embodiment, the cloud computing network 18 includes a cloud communications network 18 comprising plural different cloud component networks 72, 74, 76, 78. "Cloud computing" is a model for enabling, on-demand network access to a shared pool of configurable computing resources (e.g., public and private networks, servers, storage, applications, and services) that are shared, rapidly provisioned and released with minimal management effort or service provider interaction.

This exemplary cloud computing model for electronic information retrieval promotes availability for shared resources and comprises: (1) cloud computing essential characteristics; (2) cloud computing service models; and (3) cloud computing deployment models. However, the present invention is not limited to this cloud computing model and other cloud computing models can also be used to practice the invention.

Exemplary cloud computing essential characteristics appear in Table 1. However, the present invention is not limited to these essential characteristics and more, fewer or other characteristics can also be used to practice the invention.

TABLE 1

1. On-demand automated differential medical diagnosis services. Automatic differential medical diagnosis services can unilaterally provision computing capabilities, such as server time and network storage, as needed automatically without requiring human interaction with each network server on the cloud communications network 18, 18'.
2. Broadband network access. Automatic automated differential medical diagnosis services capabilities are available over plural broadband communications networks and accessed through standard mechanisms that promote use by heterogeneous thin or thick client platforms (e.g., mobile phones, smart phones 14, tablet computers 12, laptops, PDAs, etc.). The broadband network access includes high speed network access such as 5G wireless and/or wired and broadband and/or ultra-broad band (e.g., WiMAX, etc.) network access.
3. Resource pooling. Automatic automated differential medical diagnosis services resources are pooled to serve multiple requesters using a multi-tenant model, with different physical and virtual resources dynamically assigned and reassigned according to demand. There is location independence in that a requester of services has no control and/or knowledge over the exact location TABLE 1-continued of the provided by the automated differential medical diagnosis service
resources but may be able to specify location at a higher level of abstraction
(e.g., country, state, or data center). Examples of pooled resources include
storage, processing, memory, network bandwidth, virtual server network
device and virtual target network devices.
4. Rapid elasticity. Capabilities can be rapidly and elastically provisioned, in some
cases automatically, to quickly scale out and rapidly released to quickly scale
for automated differential medical diagnosis service collaboration. For
automated differential medical diagnosis services, multi-media collaboration
converters, the automatic automated differential medical diagnosis services
collaboration and analytic conversion capabilities available for provisioning
appear to be unlimited and can be used in any quantity at any time.
5. Measured Services. Cloud computing systems automatically control and optimize
resource use by leveraging a metering capability at some level of abstraction
appropriate to the type of automated differential medical diagnosis (e.g.,
storage, processing, bandwidth, custom electronic content retrieval
applications, etc.). Electronic automated differential medical diagnosis
collaboration conversion usage is monitored, controlled, and reported
providing transparency for both the automated differential medical diagnosis
services provider and automated differential medical diagnosis requester of the
utilized electronic content storage retrieval service.

Exemplary cloud computing service models illustrated in
FIG. 4 appear in Table 2. However, the present invention is
not limited to these service models and more, fewer or other
service models can also be used to practice the invention.

TABLE 2

1. Cloud Computing Software Applications 62 for automated differential medical
diagnosis services. (CCSA, SaaS 64). The capability to use the provider's
applications 30, 30a, 30b, 30c, 30d, 30e, 30f running on a cloud infrastructure
66. The cloud computing applications 62, are accessible from the server
network device 20 from various client devices 12, 14, 16 through a thin client
interface such as a web browser, etc. The user does not manage or control the
underlying cloud infrastructure 66 including network, servers, operating
systems, storage, or even individual application 30, 30a, 30b, 30c, 30d, 30e,
30f capabilities, with the possible exception of limited user-specific
application configuration settings.
2. Cloud Computing Infrastructure 66 for automated differential medical diagnosis.
services (CCI 68). The capability provided to the user is to provision
processing, storage and retrieval, networks 18, 72, 74, 76, 78 and other
fundamental computing resources where the consumer is able to deploy and
run arbitrary software, which can include operating systems and applications
30, 30a, 30b, 30c, 30d, 30e, 30f. The user does not manage or control the
underlying cloud infrastructure 66 but has control over operating systems,
storage, deployed applications, and possibly limited control of select
networking components (e.g., host firewalls, etc.).
3. Cloud Computing Platform 70 for automated differential medical diagnosis
services. (CCP 71). The capability provided to the user to deploy onto the
cloud infrastructure 66 created or acquired applications created using
programming languages and tools supported servers 20, 22, 24, 26, etc. The
user not manage or control the underlying cloud infrastructure 66 including
network, servers, operating systems, or storage, but has control over the
deployed applications 30a, 30b, 30c, 30d, 30e, 30f and possibly application
hosting environment configurations.

Exemplary cloud computing deployment models appear
in Table 3. However, the present invention is not limited to
these deployment models and more, fewer or other deploy-
ment models can also be used to practice the invention.

TABLE 3

1. Private cloud network 72. The cloud network infrastructure is operated solely for
automated differential medical diagnosis. It may be managed by the electronic
content retrieval or a third party and may exist on premise or off premise.
2. Community cloud network 74. The cloud network infrastructure is shared by
several different organizations and supports a specific electronic content
storage and retrieval community that has shared concerns (e.g., mission,
security requirements, policy, compliance considerations, etc.). It may be
managed by the different organizations or a third party and may exist on
premise or off premise.

TABLE 3-continued

3. Public cloud network 76. The cloud network infrastructure such as the Internet, PSTN, SATV, CATV, Internet TV, etc. is made available to the general public or a large industry group and is owned by one or more organizations selling cloud services.
4. Hybrid cloud network 78. The cloud network infrastructure 66 is a composition of two and/or more cloud networks 18 (e.g., private 72, community 74, and/or public 76, etc.) and/or other types of public and/or private networks (e.g., intranets, etc.) that remain unique entities but are bound together by standardized or proprietary technology that enables data and application portability (e.g., cloud bursting for load-balancing between clouds, etc.)

Cloud software 64 for electronic content retrieval takes full advantage of the cloud paradigm by being service oriented with a focus on statelessness, low coupling, modularity, and semantic interoperability for electronic content retrieval. However, cloud software services 64 can include various states.

Cloud storage of desired electronic content on a cloud computing network includes agility, scalability, elasticity and multi-tenancy. Although a storage foundation may be comprised of block storage or file storage such as that exists on conventional networks, cloud storage is typically exposed to requesters of desired electronic content as cloud objects.

In one exemplary embodiment, the cloud application 30, 30b, 30c, 30d, 30e, 30f, offers cloud services for automated differential medical diagnosis. The application 30, 30a, 30b, 30c, 30d, 30e, 30f offers the cloud computing Infrastructure 66, 68 as a Service 62 (IaaS), including a cloud software infrastructure service 62, the cloud Platform 70, 71 as a Service 62 (PaaS) including a cloud software platform service 62 and/or offers Specific cloud software services as a Service 64 (SaaS) including a specific cloud software service 64 for automated differential medical diagnosis. The IaaS, PaaS and SaaS include one or more of cloud services 62 comprising networking, storage, server network device, virtualization, operating system, middleware, run-time, data and/or application services, or plural combinations thereof, on the cloud communications network 18.

Figure 5:
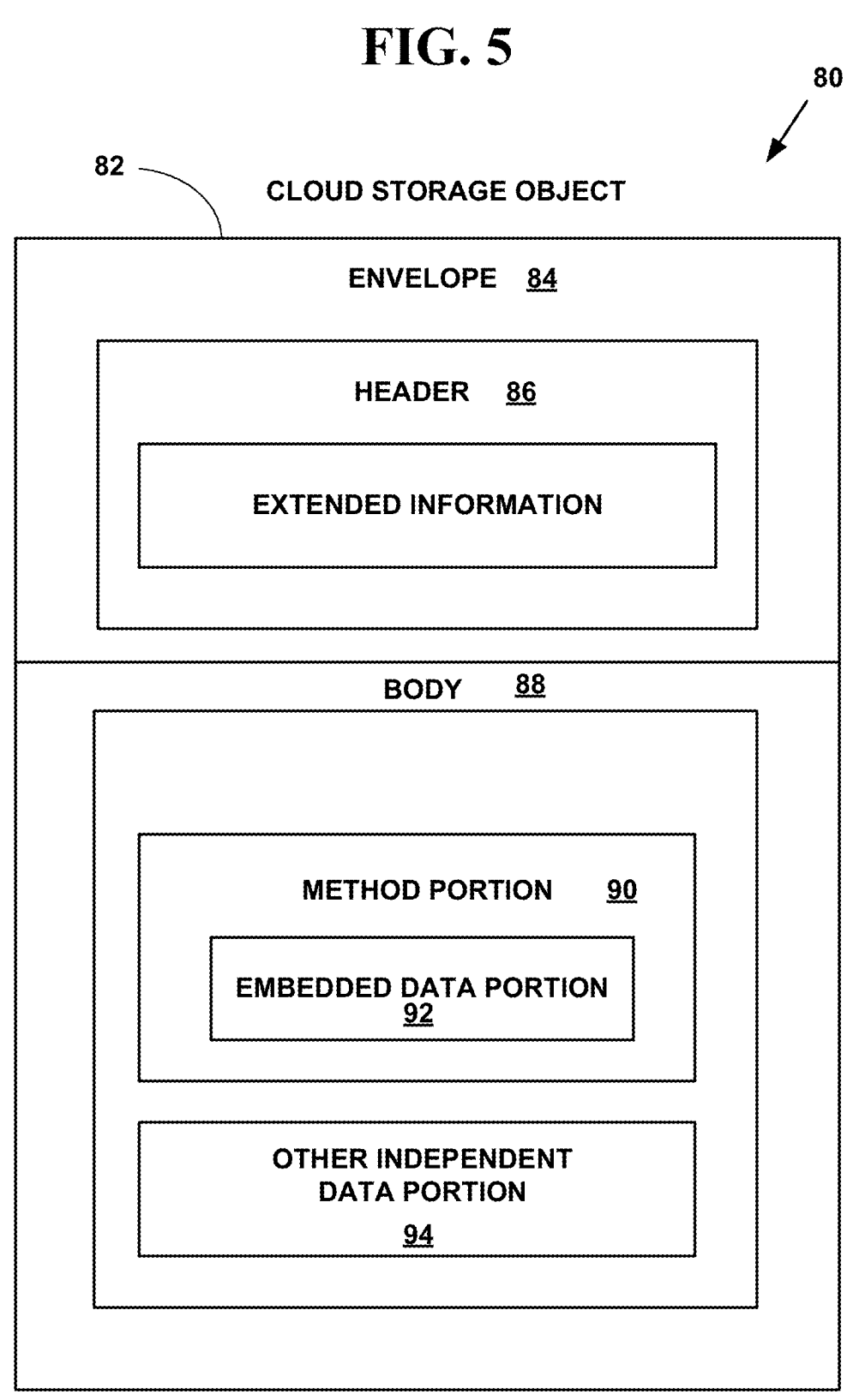
FIG. 5 is a block diagram illustrating an exemplary cloud storage object.

FIG. 5 is a block diagram 80 illustrating an exemplary cloud storage object 82. One or more server network devices (e.g., 20, 22, 24, 26, etc.) store portions 13, 13a, 15 of the electronic message content 13, 13a, 15 (e.g., SMS, MMS, RCS, etc.) as cloud storage objects 82 (FIG. 5) as is described herein.

The cloud storage object 82 includes an envelope portion 84, with a header portion 86, and a body portion 88. However, the present invention is not limited to such a cloud storage object 82 and other cloud storage objects and other cloud storage objects with more, fewer or other portions can also be used to practice the invention.

The envelope portion 84 uses unique namespace Uniform Resource Identifiers (URIs) and/or Uniform Resource Names (URNs), and/or Uniform Resource Locators (URLs) unique across the cloud communications network 18 to uniquely specify, location and version information and encoding rules used by the cloud storage object 82 across the whole cloud communications network 18. For more information, see IETF RFC-3305, Uniform Resource Identifiers (URIs), URLs, and Uniform Resource Names (URNs), the contents of which are incorporated by reference.

The envelope portion 84 of the cloud storage object 82 is followed by a header portion 86. The header portion 86 includes extended information about the cloud storage objects such as authorization and/or transaction information, etc.

The body portion 88 includes methods 90 (i.e., a sequence of instructions, etc.) for using embedded application-specific data in data elements 92. The body portion 88 typically includes only one portion of plural portions of application-specific data 92 and independent data 94 so the cloud storage object 82 can provide distributed, redundant fault tolerant, security and privacy features described herein.

Cloud storage objects 82 have proven experimentally to be a highly scalable, available and reliable layer of abstraction that also minimizes the limitations of common file systems. Cloud storage objects 82 also provide low latency and low storage and transmission costs.

Cloud storage objects 82 are comprised of many distributed resources, but function as a single storage object, are highly fault tolerant through redundancy and provide distribution of desired electronic content across public communication networks 76, and one or more private networks 72, community networks 74 and hybrid networks 78 of the cloud communications network 18. Cloud storage objects 82 are also highly durable because of creation of copies of portions of desired electronic content across such networks 72, 74, 76, 78 of the cloud communications network 18. Cloud storage objects 82 includes one or more portions of desired electronic content and can be stored on any of the 72, 74, 76, 78 networks of the cloud communications network 18. Cloud storage objects 82 are transparent to a requester of desired electronic content and are managed by cloud applications 30, 30a, 30b, 30c, 30d, 30e, 30f.

In one embodiment, cloud storage objects 82 are configurable arbitrary objects with a size up to hundreds of terabytes, each accompanied by with a few kilobytes of metadata. Cloud objects are organized into and identified by a unique identifier unique across the whole cloud communications network 18. However, the present invention is not limited to the cloud storage objects described, and more fewer and other types of cloud storage objects can be used to practice the invention.

Cloud storage objects 82 present a single unified namespace or object-space and manages desired electronic content by user or administrator-defined policies storage and retrieval policies. Cloud storage objects includes Representational state transfer (REST), Simple Object Access Protocol (SOAP), Lightweight Directory Access Protocol (LDAP) and/or Application Programming Interface (API) objects and/or other types of cloud storage objects. However, the present invention is not limited to the cloud storage objects described, and more fewer and other types of cloud storage objects can be used to practice the invention.

REST is a protocol specification that characterizes and constrains macro-interactions storage objects of the four components of a cloud communications network 18, namely origin servers, gateways, proxies and clients, without imposing limitations on the individual participants.

SOAP is a protocol specification for exchanging structured information in the implementation of cloud services with storage objects. SOAP has at least three major characteristics: (1) Extensibility (including security/encryption, routing, etc.); (2) Neutrality (SOAP can be used over any transport protocol such as HTTP, SMTP or even TCP, etc.), and (3) Independence (SOAP allows for almost any programming model to be used, etc.)

LDAP is a software protocol for enabling storage and retrieval of electronic content and other resources such as files and devices on the cloud communications network 18. LDAP is a "lightweight" version of Directory Access Protocol (DAP), which is part of X.500, a standard for directory services in a network. LDAP may be used with X.509 security and other security methods for secure storage and retrieval. X.509 is public key digital certificate standard developed as part of the X.500 directory specification. X.509 is used for secure management and distribution of digitally signed certificates across networks.

An API is a particular set of rules and specifications that software programs can follow to communicate with each other. It serves as an interface between different software programs and facilitates their interaction and provides access to automatic automated differential medical diagnosis in a cloud or non-cloud environment. In one embodiment, the API for automated differential medical diagnosis is available to network devices 12, 14, 16, 20, 22, 24, 26, 31, 98-104 and networks 18, 18'. However, the present invention is not limited to such an embodiment and other embodiments can be used to practice the invention.

Wearable Devices

Wearable technology" and/or "wearable devices" are clothing and accessories incorporating computer and advanced electronic technologies. Wearable network devices provide several advantages including, but not limited to: (1) Quicker access to notifications. Important and/or summary notifications are sent to alert a user to view the whole message. (2) Heads-up information. Digital eye wear allows users to display relevant information like directions without having to constantly glance down; (3) Always-on Searches. Wearable devices provide always-on, hands-free searches; and (4) Recorded data and feedback. Wearable devices take telemetric data recordings and providing useful feedback for users for exercise, health, fitness, etc. activities.

Figure 6:
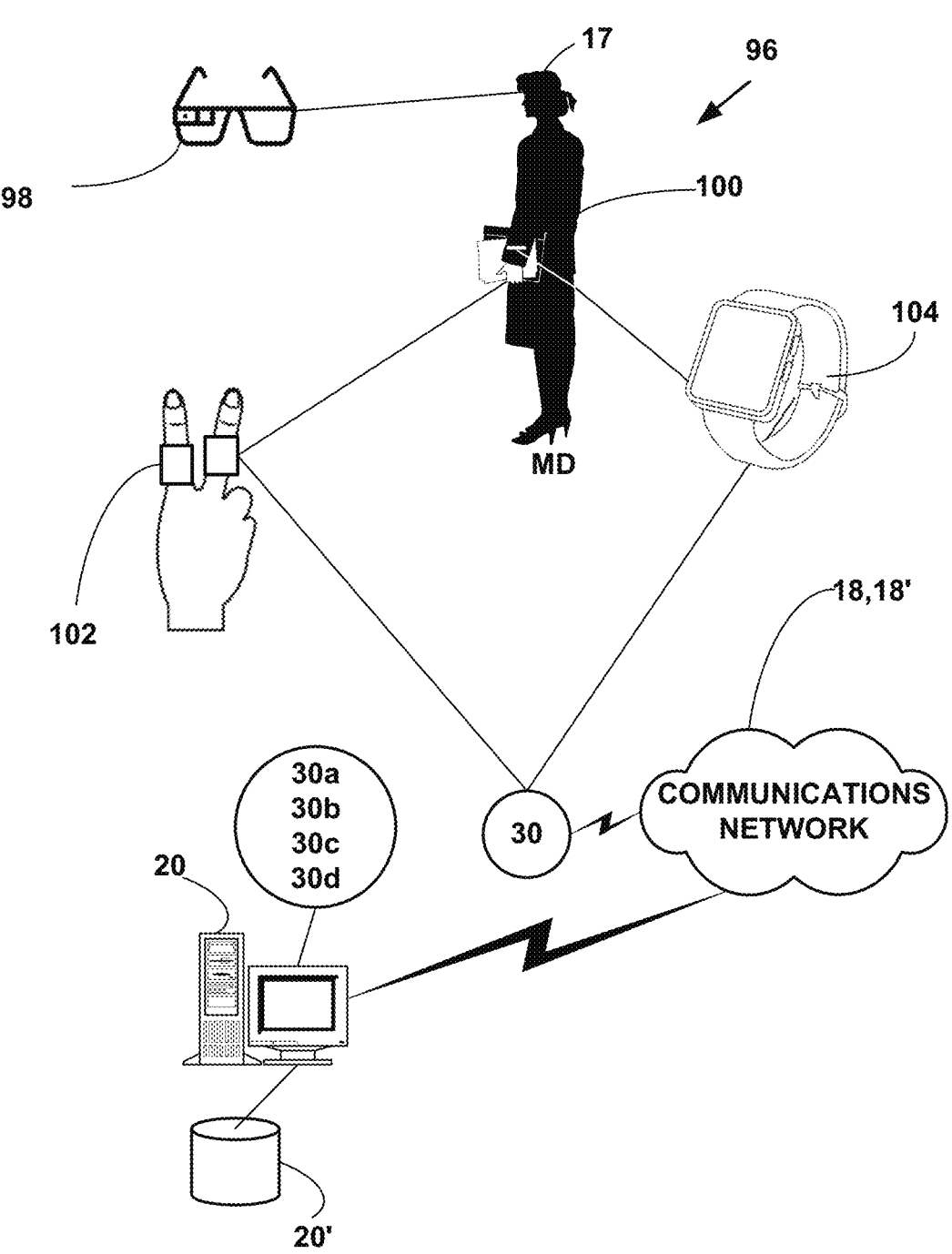
FIG. 6 is a block diagram illustrating wearable network devices.

FIG. 6 is a block diagram with 96 illustrating wearable devices. The wearable devices include one or more processors and include, but are not limited to, wearable digital glasses 98, clothing 100, jewelry 102 (e.g., smart rings, smart earrings, etc.) and/or watches 104. However, the present invention is not limited to such embodiments and more, fewer and other types of wearable devices can also be used to practice the invention.

In one specific embodiment, the application 30, 30a, 30b, 30c, 30d, 30e, 30f interacts with wearable devices 98-104 automatic automated differential medical diagnosis the methods described herein. However, the present invention is not limited this embodiment and other embodiments can also be used to practice the invention.

Artificial Intelligence (AI) and Big Data

"Artificial intelligence" (AI), also known as machine intelligence (MI), is intelligence demonstrated by machines, in contrast to the natural intelligence (NI) displayed by humans and other animals. AI research is defined as the study of "intelligent agents." Intelligent agents are any software application or hardware device that perceives its environment and takes actions that maximize its chance of successfully achieving its goals. Colloquially, the term "artificial intelligence" is applied when a machine mimics "cognitive" functions that humans associate with human brains, such as learning, problem solving and comparing large number of data points.

In one embodiment, the present invention uses one or more AI methods including, but are not limited to, AI knowledge-based methods 30b for automated differential medical diagnosis. However, the present invention is not limited to such an embodiment and more, fewer and/or other AI methods can be used to practice the invention.

In one embodiment, the medical diagnosis application 30a includes an integral AI application 30b and a Big Data set application 30c. In another embodiment, the medical diagnosis application 30a includes separate AI application 30b and a Big Data set application 30c. However, the present invention is not limited to such an embodiment and more, fewer and/or other combinations can be used to practice the invention.

In one embodiment, SaaS 64 includes an AI application 30b with the AI methods described herein. In another embodiment, the AI application 30b is a standalone application. However, the present invention is not limited to such an embodiment, and the AI application 30b can be provided in other than the SaaS 64. However, the present invention is not limited to such an embodiment and more, fewer and/or other combinations can be used to practice the invention.

"Big Data" refers to the use of predictive analytic methods that extract value from data, and to a particular size of data set. The quantities of data used are very large, at least 100,000 data points and more typically 500,000 to one Million+ data points. Analysis of Big Data sets are used to find new correlations and to spot trends. In one embodiment, the AI application 30b includes a Big Data set application 30c with the Big Data set described herein. In one embodiment, SaaS 64 includes and Big Data application 30d with the Big Data described herein. However, the present invention is not limited to such an embodiment and more, fewer and/or other combinations can be used to practice the invention.

In one embodiment, the AI methods described herein collect data information to create and store (e.g., in cloud storage object 82, etc.) a Big Data that is used to analyze trends find new correlations and to spot trends. However, the present invention is not limited to such an embodiment and the AI methods described herein can be used without Big Data sets.

Short Message Service (SMS) Messaging

Short Message Service (SMS) is an electronic text messaging service component of phone, Web, or mobile communication systems. It uses standardized communications protocols to allow fixed line or mobile phone devices to exchange short text messages.

SMS messages were defined in 1985 as part of the Global System for Mobile Communications (GSM) series of standards as a means of sending messages of up to 160 characters to and from GSM mobile handsets. Though most SMS messages are mobile-to-mobile text messages, support for the service has expanded to include other mobile technologies as well as satellite and landline networks.

The SMS Internet Engineering Task Force (IETF) Request for Comments (RFC) 5724, ISSN: 2070-1721, 2010, is incorporated herein by reference.

Direct and Instant Messages

A "direct message" (DM) is a private form of communication between social media users that is only visible to the sender and recipient(s). INSTAGRAM, TWITTER, FACE- BOOK and other platforms, allow for direct messages between their users, with varying restrictions by platform.

An "instant message" (IM) is a type of online chat allowing real-time text transmission over the Internet or another computer network. Messages are typically transmitted between two or more parties, when each user inputs text and triggers a transmission to the recipient, who are all connected on a common network Multimedia Messaging Service (MMS)

Multimedia Messaging Service (MMS) is a standard way to send messages that include multimedia content to and from a mobile phone over a cellular network. Users and providers may refer to such a message as a PXT, a picture message, and/or a multimedia message.

The MMS Internet Engineering Task Force (IETF) Request for Comments (RFC) 4355 and 4356, are incorporated herein by reference.

Rich Communication Suite (RCS)

Rich Communications Suite/Rich Communications System (RCS) is a communication protocol between mobile telephone carriers, between phones and carriers, and between individual devices aiming at replacing SMS messages with a message system that is richer, provides phonebook polling (e.g., for service discovery, etc.), and can transmit in-call multimedia. It is also marketed under the names of Advanced Messaging, Advanced Communications, Chat, joyn, Message+ and SMS+. RCS is also a communication protocol available for device-to-device (D2D) exchanges without using a telecommunications carrier for devices that are in close physical proximity (e.g., between two IoT devices, smart phones, smart phone and electronic tablet, etc.)

One advantage RCS Messaging has over SMS is that RCS enables users to send rich, verified messages including photos, videos and audio messages, group messages, read receipts, indicators to show other users are typing a message, carousel messages, suggested chips, chat bots, barcodes, location integration, calendar integration, dialer integration, and other RCS messaging features. RCS messaging includes person-to-person (P2P), application-to-person (A2P), application-to-application (A2A), application-to-device (A2D) and/or device-to-device (D2D) messaging.

The RCS Interworking Guidelines Version 14.0, 13 Oct. 2017, GSM Association, Rich Communication Suite RCS API Detailed Requirements, version 3.0, Oct. 19, 2017, Rich Communication Suite 8.0 Advanced Communications Services and Client Specification Version 9.0, 16 May 2018, RCS Universal Profile Service Definition Document Version 2.2, 16 May 2018, and Rich Communication Suite Endorsement of OMA CPM 2.2 Conversation Functions Version 9.0, 16 Oct. 2019, are all incorporated herein by reference.

The Rich Communication Suite-Enhanced (RCS-e) includes methods of providing first stage interoperability among Mobile Network Operators (MNOs). RCS-e is a later version of RCS which enables mobile phone end users to use instant messaging (IM), live video sharing and file transfer across any device on any MNO.

The RCS functionality of the present invention includes, but is not limited to, one and two-way, rich, verified, multimedia messages including photos, videos and audio messages, group messages, read receipts, indicators to show other users are typing a message, predefined quick-reply suggestions, rich cards, carousels, action buttons, maps, click-to-call, calendar integration, geo-location, etc. The RCS functionality also includes RCS emulators and/or thin RCS applications that provide full and/or selected features of available RCS functionality.

Complaints of a Specific Patient at a Medical Facility

One or more patient complaints are collected for a patient 19 at a medical facility 21 by collecting patient history (HX) information with medical doctors, nursing staff, nurse practitioners, medical assistants, and/or other medical staff. The one or more patient complaints are used by a medical diagnosis application 30a using one or more automated diagnosis methods to determine a final diagnosis 13', one or more differential diagnoses 13d and/or one or more critical differential diagnoses and a final treatment plan for the specific patient 19 at the medical facility 21. However, the present invention is not limited to such an embodiment and other embodiments and other HX information can be used to practice the invention.

The HX information typically includes, but is not limited to appropriate history of present illness ("HPI"), review of systems ("ROS"), past medical family social history ("PMSFH"), review of system ("ROS") information allergies, medications, vital signs, etc. This information may or may not be modified by or for the medical facility that collected the patient encounter information.

Table 4 illustrates exemplary HX information collected. However, the present invention is not limited to this HX information, more, less and other types of HX information can also be collected from the patient encounter information.

TABLE 4

HX Information

Chief Complaint (CC):
Description of one or more problems (e.g., sore throat, chest pains, trouble breathing, fever, etc.)
History of Present Illness (HPI):
Location; quality; severity; duration; timing; context; modifying factors; associated signs and symptoms.
Past medical, family, social history (PFMSH):
Medical History - the patient's past experiences with illnesses, operations, injuries and treatments.
Family History - a review of medical events in the patient's family, including diseases which may be hereditary or place the patient at risk.
Social History - an age appropriate review of past and current activities.
Review of Systems (ROS):
Constitutional; eyes, ears, nose, mouth, throat; cardio-vascular; respiratory; GI; GU; muscular; neurological; psychological; immune; etc.

Another set of patient encounter information physical examination information ("PX") obtained from the patient encounter. Table 5 illustrates where body areas and organ systems from which PX information is collected. However, the present invention is not limited to this PX information, more, less and other types of PX information can also be collected from the patient encounter information.

TABLE 5

PX Areas

Body Areas:
Head, including face; Back including spine; Chest including breasts; Genitalia including groin and buttocks; Abdomen; Neck; Extremities; etc.
Organ Systems:
Constitutional; eyes, ears, nose, mouth, throat; cardio-vascular; respiratory; GI; GU; muscular; neurological; psychological; immune; etc.

Table 6 illustrates possible levels of the physical exam types of PX information determined. This example uses one specific set of guidelines commonly referred to and published by the Centers for Medicare & Medicaid Services ("CMS") as Documentation Guidelines for Evaluation and Management Services, but can utilize other methods or guidelines as determined by the type of exam or by changes in prescribed or allowable guidelines. In addition, the PX information is exemplary only, and the present invention is not limited to such PX information.

TABLE 6

| PX Types | |
|---|---|
| PF | One to five elements identified (e.g., one to five body areas or organs) |
| EXPF | At least six elements identified (e.g., up to a total of six organ systems) |
| DET | At least twelve items identified from 2 (or more) PX areas |
| COMP | Two or more elements identified in nine or more organ systems. |

The PX types include, but are not limited to: a problem focused ("PF") exam that includes 1-5 specific exam elements identified; an expanded problem focused exam ("EXPF") that includes at least 6 specific exam elements; Detailed exam ("DET") that includes at least 12 elements in two or more areas/systems, and a comprehensive exam ("COMP") that includes documentation of at least two elements from each of nine areas/systems.

Another set of patient encounter information used is complexity of medical decision-making information ("CX") obtained from the patient encounter. The CX information includes a number of diagnosis ("DX") or treatment options and risk ("RISK") information. However, the present invention is not limited to this embodiment and other types of extracted complexity information can be used to practice the invention.

Table 7 illustrates exemplary CX information. However, the present invention is not limited to this embodiment and other embodiments can also be used to practice the invention.

TABLE 7

| CX Types | |
|---|---|
| DX | RISK |
| straight forward ("SF") number of diagnosis, <= one. | straight forward risk ("SF"), includes a self-limited or minor problem. |
| low number of diagnoses ("LOW"), minimal. | low risk ("LOW"), includes two or more minor problems, one stable chronic illness or an acute uncomplicated illness or injury. |
| moderate number of diagnoses ("MOD"), multiple. | moderate ("MOD") includes one or more chronic illnesses with mild exacerbation, progression, or side effect treatment, two or more stable chronic illnesses, an undiagnosed new problem with uncertain prognosis or an acute illness with systemic symptoms or an acute complicated injury. |
| high number of possible diagnoses ("HIGH"), extensive. | high risk ("HIGH"), includes one or more chronic illnesses with severe exacerbation, progression or side effects of treatment, or acute or chronic |

TABLE 7-continued

| CX Types | |
|---|---|
| DX | RISK |
| | illnesses or injuries that may pose a threat to life or bodily function or an abrupt change in neurological status. |

The DX information includes, but is not limited to: straight forward ("SF") diagnosis; a low number of diagnoses ("LOW"); a moderate number of diagnoses ("MOD"); and a high number of possible diagnoses ("HIGH"). This DX scoring can be performed using an objective scoring system. A unique aspect of this invention includes (but is not limited to) presentation of these choices in check-box form with each of a maximum number of choices in each category represented by a check-box. Scoring of the DX section can then be performed by adding a point value of each box to obtain the total score in the DX section. Although, scoring of the DX section is not limited to this method, if it is used the following scores correlate with the various levels of DX: ($\leq 1$) minimal; (2) limited; (3) multiple; or (4) extensive.

The RISK information includes: minimal or straight forward ("SF") risk in which the medical problem is self-limited or a minor problem (e.g., cold, insect bite, etc.); low risk ("LOW") in which the medical problem includes two or more minor problems, one stable chronic illness (e.g., well controlled hypertension or non-insulin dependent diabetes, cataract, etc.) or an acute uncomplicated illness or injury (allergic reaction, simple sprain); moderate risk ("MOD") in which the medical problem includes one or more chronic illnesses with mild exacerbation, progression, or side effect treatment, two or more stable chronic illnesses, an undiagnosed new problem with uncertain prognosis (e.g., lump in breast or prostrate, etc.) an acute illness with systemic symptoms (e.g., pneumonitis, colitis, etc.) or an acute complicated injury (e.g., head injury with brief loss of consciousness): and high risk ("HIGH") in which the medical problem includes one or more chronic illnesses with severe exacerbation, progression or side effects of treatment, or acute or chronic illnesses or injuries that may pose a threat to life or bodily function (e.g., multiple trauma, acute MI, pulmonary embolus, severe respiratory distress, progressive severe rheumatoid arthritis, psychiatric illness with potential threat to self or others, acute renal failure, etc.) or an abrupt change in neurological status (e.g., seizure, TIA, weakness or sensory loss, etc.).

Automated Differential Medical Diagnosis

Determining a final diagnosis and one or more differential diagnoses from a patient encounter is complex and presents many risks, even for an experienced medical doctor. There is a significant risk of complications, morbidity, mortality, and/or comorbidity associated with the patient's complaints due to misdiagnoses of medical problems associated with the patient complaints. A patient risk diagnosis is based on the patient's current health status, past health history, and other risk factors that may increase the patient's likelihood of experiencing a health problem. Patient complications are defined as unsuspected medical conditions that arise during the treatment of a patient. Patient morbidity is defined as a patient having a disease or a symptom of a disease. Comorbidity occurs when a person has more than one disease or condition at the same time and are often chronic or long-term conditions considered pre-existing conditions.

The present invention significantly reduces a complexity and risk at plural different levels associated with determining a final diagnosis and one or more differential diagnoses from a from a patient encounter.

FIGS. 7A, 7B, 7C and 7D are a flow diagram illustrating a Method 106 for providing automated differential medical diagnosis.

In FIG. 7A at Step 108, displaying from a medical diagnosis application on a server network device with one or more processors, a list of plural patient complaints from a database for one or more patient complaints received at a medical facility, on a network device with one or more processors via a communications network on a secure connection. At Step 110, receiving a first message on the medical diagnosis application on the server network device including the one or more patient complaints for a specific patient at the medical facility from the network device with via the communications network on the secure connection. At Step 112, displaying from the medical diagnosis application on the server network device, a list of a possible diagnoses related to the one or more patient complaints for the specific patient on the network device via the communication network on the secure connection, the list of possible diagnoses related to the one or more patient complaints including: (1) a check box to include differential diagnoses for the one or more patient complaints including a differential name and differential diagnosis description, (2) a diagnosis code (Dx), (3) a delete diagnosis icon to remove a diagnosis that does not apply to the specific patient from the list, and (4) an add diagnosis link including a link to a list of additional related diagnoses that could apply to the specific patient including one or more electronic links to add additional diagnoses to the list of plural patient complaints displayed for the one or more patient complaints received in the first message. The list of possible differential diagnoses reducing a first complexity level and a first risk level associated with determining a primary diagnosis and one or more differential diagnoses related to the one or more patient complaints for the specific patient.

In FIG. 7B at Step 114, receiving a second message on the medical diagnosis application on server network device including one or more selection inputs with diagnosis information selected for the one or more patient complaints for the specific patient at the medical facility from the network device with via the communications network on the secure connection. At Step 116, displaying from the medical diagnosis application on server network device, diagnosis information and differential diagnosis information related to the one or more patient complaints for the specific patient on the network device via the communication network on the secure connection; the diagnosis and differential diagnosis information including: (1) a determined diagnosis section including a graphical checkbox to add the determined diagnosis as a final diagnosis for the one or more patient complaints for the specific patient at the medical facility, (2) a differential diagnosis section including a graphical checkbox to add one or more differential diagnoses for the specific patient at the medical facility, (3) a diagnosis name including a diagnosis description and an International Classification of Diseases (ICD) diagnostic code, (4) a list of evaluation methods used to include and rule out one or more differential diagnoses and select a final diagnosis, (5) a diagnosis (Dx) morbidity threat including plural of morbidity threat levels for the one or more differential diagnoses, and (6) a graphical search electronic link to search for additional diagnoses to add to the likely differential diagnosis list.

In FIG. 7C at Step 118, receiving a third message on the medical diagnosis application on server network device including one or more selection inputs with differential diagnosis information selected for the one or more patient complaints for the specific patient at the medical facility from the network device with via the communications network on the secure connection. At Step 120, determining on the medical diagnosis application on server network device with one or more diagnosis methods with information from the first message, second message and third message: (1) final diagnosis information including a final diagnosis for the one or more patient complaints for the specific patient at the medical facility, and (2) differential diagnosis information including one or more likely differential diagnoses and one or more critical differential diagnoses for the specific patient at the medical facility. At Step 122, creating on the medical diagnosis application on server network device with the one or more diagnosis methods with information from the first message, second message and third message: (1) an electronic visit summary for the specific patient at the medical facility supplied to the specific patent at the medical facility including the determined final diagnosis information and differential diagnosis information, (2) a new medical record for the specific patient at the medical facility including the determined final diagnosis information and differential diagnosis information, and (3) a treatment plan for the specific patent at the medical facility including the determined final diagnosis information and differential diagnosis information. The created electronic visit summary, the created new medical record and the created treatment plan, reducing a second complexity level and a second risk level associated with determining a final diagnosis, one or more differential diagnoses created for the one or more patient complaints for the specific patient at the medical facility.

In FIG. 7D at Step 124, storing from the medical diagnosis application on server network device the determined final diagnosis information and differential diagnosis information, the created electronic visit summary, the new medical record and the created treatment plan for the specific patent at the medical facility in the database. At Step 126, displaying from the medical diagnosis application on server network device, diagnosis summary information related to the one on more patient complaints for the specific patient at medical facility on the network device via the communication network on the secure connection. The diagnosis summary information including: final diagnosis information including: (1) the final diagnosis for the one or more patient complaints for the specific patient at the medical facility, (2) the differential diagnosis information including one or more likely differential diagnoses and critical differential diagnoses for the specific patient at the medical facility. (3) the created electronic visit summary for the specific patient at the medical facility supplied to the specific patent at the medical facility, (4) the created new medical record for the specific patient at the medical facility supplied to the specific patent at the medical facility, and (5) the created treatment plan for the specific patient. At step 128, sending a fourth message from the medical diagnosis application on server network device to the server network device via the communication network on the secure connection. The fourth message including the created electronic visit summary, the created new medical record and the created treatment plan for the specific patient at the medical facility.

Method 106 is illustrated with an exemplary embodiment. However, the present invention is not limited to such an embodiment and other embodiments may be used to practice the invention.

In such an exemplary embodiment in FIG. 7A at Step 108, displaying from a medical diagnosis application 30*a* on a server network device 20, 22, 24, 26 with one or more processors, a list of plural patient complaints from a database 20', 22', 24', 26' for one or more patient complaints 13 received at a medical facility 21, on a network device 12, 14, 16, 20, 22, 24, 26, 31, 33, 98-104 with one or more processors via a communications network 18, 18' on a secure connection 23.

In one embodiment, the medical facility 21, includes, but is not limited to, an emergency room at a hospital, an urgent care facility, a medical clinic, a doctor's office, a telemedicine connection over the communications network 18, 18' and/or other type of medical facilities. However, the present invention is not limited to such an embodiment and more, fewer and/other types of medical facilities 21 may be used to practice the invention.

In one embodiment, the plural patient complaints include, but are not limited to, coughs, fevers, pains in various parts of the body, shortness of breath, dizziness, broken bones, sprains, cuts, puncture wounds, comorbidity (e.g., pre-existing conditions, such as diabetes, heart disease, cancer, etc.). However, the present invention is not limited to such an embodiment and more, fewer and/other types of patient complaints, may be used to practice the invention.

In one embodiment, the server network device 20, 22, 24, 26 is replaced with a target network device 12, 14, 16, 31, 33, 98-104 including a medical diagnosis application 30 and/or 30*a*. However, the present invention is not limited to such an embodiment and other embodiments can be used to practice the invention.

In one embodiment, network device includes target network devices 12, 14, 16, 31, 33, 98-104 and/or another server network device 20, 22, 24, 26. However, the present invention is not limited to such an embodiment and other embodiments can be used to practice the invention.

In one embodiment, medical diagnosis application 30*a* comprises a cloud communications network 18 SaaS 64 on a cloud server network device. However, the present invention is not limited to such an embodiment and other embodiments can be used to practice the invention.

At Step 110, receiving a first message on the medical diagnosis application 30*a* on server network device 20, 22, 24, 26 including the one or more patient complaints 13 for the specific patient 19 at the medical facility 21 from the network device 12, 14, 16, 20, 22, 24, 26, 31, 33, 98-104 with via the communications network 18, 18' on the secure connection 23.

In one embodiment, the one or more patient complaints 13 for the specific patients include the HX and other information described in Tables 4-7 above. However, the present invention is not limited to such an embodiment and other embodiments can be used to practice the invention.

Figure 8:
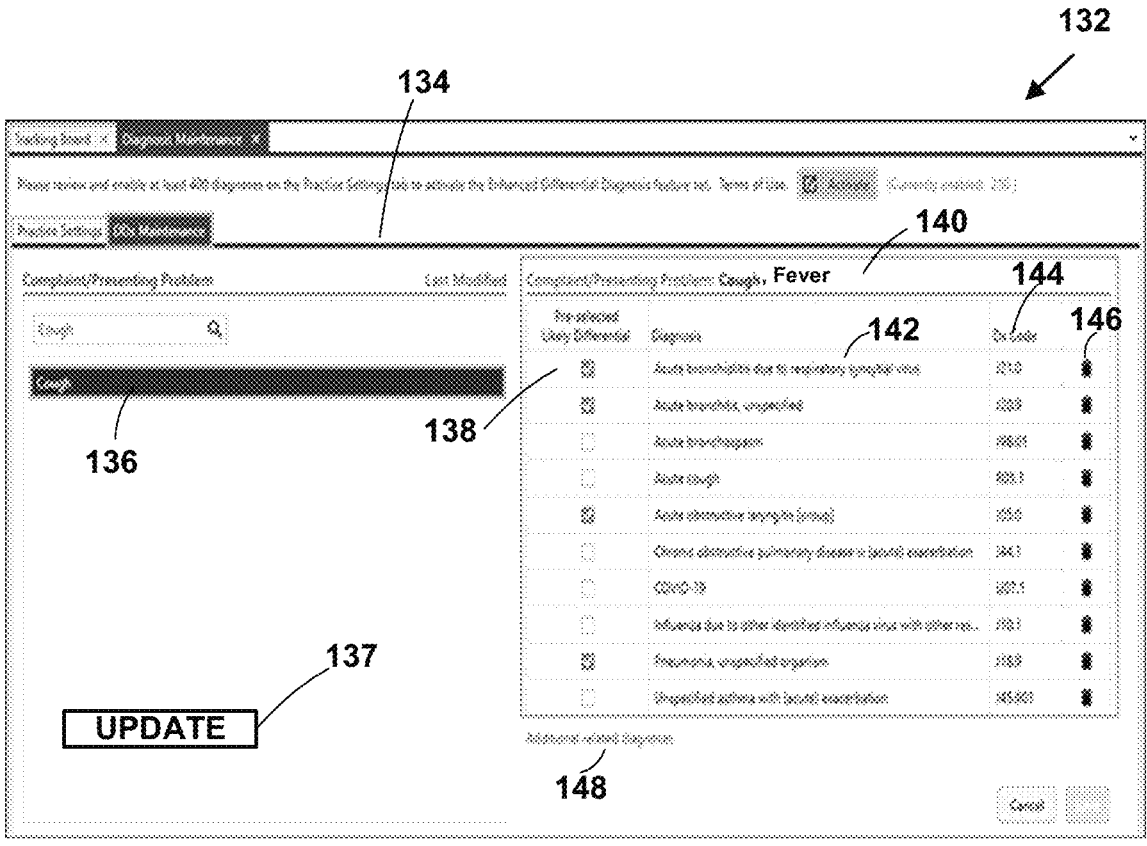
FIG. 8 a block diagram illustrating an exemplary chief complaint display screen.

FIG. 8 a block diagram 132 illustrating an exemplary chief complaint display screen 134.

FIG. 8 illustrates (1) a patient complaint 136 (e.g., cough, with fever, dizziness, may be abnormal blood sugar level, etc.), plural check boxes 138 to include a differential diagnosis for the patient complaint 136 with a list for pre-selected likely differential diagnoses 140 for the patient complaint 136 including a diagnosis description 142, (2) a diagnosis code (Dx) 144, (3) a delete diagnosis icon 146 to remove a diagnosis that does not apply to the specific patient 19 from the list, and (4) an add diagnosis link 148 including a link to a list of additional related diagnoses that could apply to the specific patient 19 including one or more electronic links to add additional diagnoses to the list of plural patient complaints 136 displayed for the one or more patient complaints 13 received in the first message. However, the present invention is not limited to such an embodiment, and other embodiments, with more, fewer and other display screen items 134 can be used to practice the invention.

Returning to FIG. 7A at Step 110, displaying from the medical diagnosis application 30*a* on the server network device 20, 22, 24, 26, a list of a possible diagnoses related to the one or more patient complaints 13 for the specific patient 19 on the network device 12, 14, 16, 20, 22, 24, 26, 31, 33, 98-104 via the communication network 18, 18' on the secure connection 23, the list of possible diagnoses 136 related to the one or more patient complaints 13 including plural check boxes to select relevant differential diagnosis, including: (1) a check box 138 to include differential diagnoses for the one or more patient complaints 140 (e.g., e.g., cough, with fever, dizziness, may be abnormal blood sugar level, etc.) including a differential diagnosis name 142 and differential diagnosis description 144, (2) a diagnosis code (Dx) 144, (3) a delete diagnosis icon 146 to remove a diagnosis that does not apply to the specific patient from the list, and (4) an add diagnosis link 148 including a link to a list of additional related diagnoses that could apply to the specific patient 19 including one or more electronic links to add additional differential diagnoses to the list of a plural patient complaints 136 displayed for the one or more patient complaints 13 received in the first message. The list of possible differential diagnoses 140 reducing a first complexity level and a first risk level associated with determining a primary diagnosis and one or more differential diagnoses related to the one or more patient complaints 13 for the specific patient 19.

On average, medical researchers estimate that 11% of patient complaints 13 result in a misdiagnosis. Medical diagnosis application 30*a* helps reduce this 11% risk. Since the medical diagnosis application 30*a* on the server network device 20, 22, 24, 26 provides a list a list of a possible diagnoses 136 and related possible differential diagnoses 140 related to the one or more patient complaints 13 for the specific patient 19, a first complexity level and a first risk level is significantly reduced because a medical doctor 17 trying to determine a diagnosis for the specific patient 19 is presented with a comprehensive, integrated interface with the medical diagnosis application 30*a* that helps prevent the medical doctor 19 from missing and/or not considering important and relevant possible diagnoses and related possible differential diagnoses related to the one or more patient complaints 13 for the specific patient 19.

In FIG. 7B at Step 114, receiving a second message on the medical diagnosis application 30*a* on server network device 20, 22, 24, 26 including one or more selection inputs with diagnosis information selected for the one or more patient complaints 13 for the specific patient 19 at the medical facility 21 from the network device 12, 14, 16, 20, 22, 24, 26, 31, 33, 98-104 with via the communications network 18, 18' on the secure connection 23.

Figure 9:
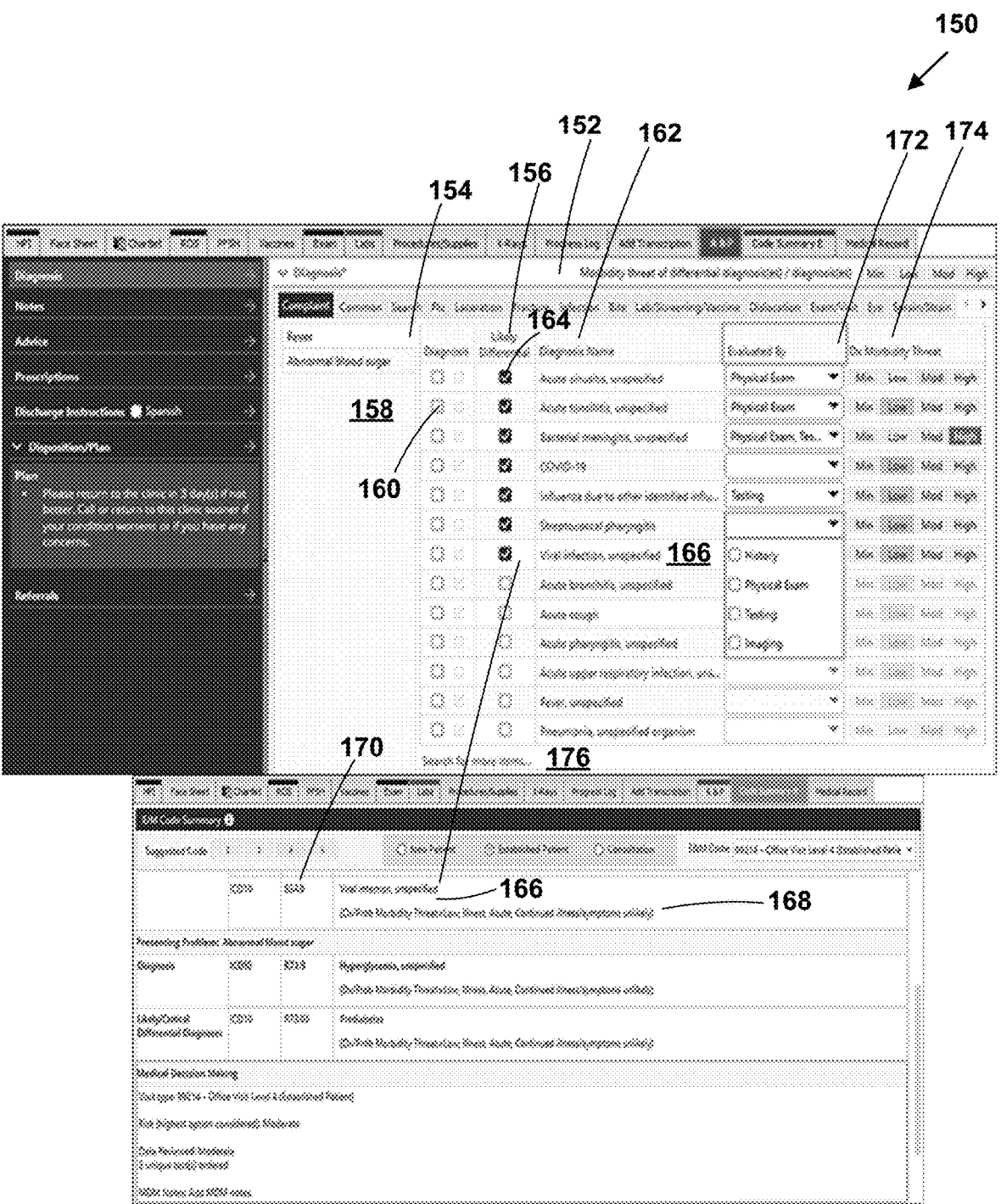
FIG. 9 is a block diagram illustrating an exemplary differential diagnosis display screen.

FIG. 9 is a block diagram 150 illustrating an exemplary differential diagnosis display screen 152.

FIG. 9 illustrates diagnosis 154 and differential diagnosis information 156 is displayed including: (1) a determined diagnosis section 158 (e.g., fever, abnormal blood sugar, etc.) including a graphical checkbox 160 to add the determined diagnosis as a final diagnosis 13' for the one or more patient complaints 13 for the specific patient 19 at the medical facility 21, (2) a differential diagnosis section 162 including a graphical checkbox 164 to add one or more differential diagnoses for the specific patient 19 at the medical facility 21. (3) a diagnosis name 166 including a diagnosis description 168 and an International Classification of Diseases (ICD) diagnostic code 170, (4) a list of evaluation methods 172 used to include and rule out one or more differential diagnoses 162 and select a final diagnosis. (5) a diagnosis (Dx) morbidity threat 174 including plural morbidity threat levels for the diagnosis, and (6) a graphical search electronic link 176 to search for additional diagnoses to add to the likely differential diagnosis list.

Returning to FIG. 7B at Step 116, displaying from the medical diagnosis application 30a on server network device 20, 22, 24, 26, diagnosis information 154 and differential diagnosis information 156 related to the one or more patient complaints 13 for the specific patient 19 on the network device 12, 14, 16, 20, 22, 24, 26, 31, 33, 98-104 via the communication network 18, 18' on the secure connection 23; the diagnosis and differential diagnosis information including: (1) a determined diagnosis section 158 (e.g., fever, abnormal blood sugar, etc.) including a graphical checkbox 160 to add the determined diagnosis as a final diagnosis for the one or more patient complaints 13 for the specific patient 19 at the medical facility 21, (2) a differential diagnosis section 162 including a graphical checkbox 164 to add one or more differential diagnoses for the specific patient 19 at the medical facility 21, (3) a diagnosis name 166 including a diagnosis description 168 and an International Classification of Diseases (ICD) diagnostic code 170 (e.g., 834.9, etc.) (4) a list of evaluation methods 172 used to include and rule out one or more differential diagnoses 162 and select a final diagnosis, (5) a diagnosis (Dx) morbidity threat 174 including plural morbidity threat levels for the differential diagnosis (e.g., low for viral infection unspecified 166), and (6) a graphical search electronic link 176 to search for additional diagnoses to add to the likely differential diagnosis list.

In one embodiment, the International Classification of Diseases (ICD) diagnostic codes, include, but are not limited to, The International Classification of Diseases (ICD), Tenth Revision (ICD-10) and/or ICD Revision 11 (ICD-11), both of which are incorporated herein by reference. ICD-10 and ICD-11 ire designed to promote international comparability in the collection, processing, classification, and presentation of mortality statistics. This includes providing a format for reporting causes of death on the death certificate. In such and embodiment, the ICD-10 and/or ICD-11 information is stored in the databases 20', 22', 24', 26' and/or in one or more cloud storage objects 82 in one or more cloud databases and/or obtained directly when needed from web-sites on the communications network 18, 18'. In another embodiment, the ICD-10 and/or ICD-11 information is stored remotely on other network devices and is accessible to the medical diagnosis application 30a on server network device 20, 22, 24, 26 via the communications network 18, 18'. However, the present invention is not limited to using ICD-10 and other embodiments with other classification of diseases can be used to practice the invention.

In one embodiment, the list of evaluation methods 172 used to include and rule out one or more differential diagnoses 162 and select a final diagnosis 13' includes, but is not limited to using one or more of, and/or a combination of: a prior and/or current medical history of the patient 19, a prior and/or current physical exam of the patent 19, prior and/or current diagnostic testing (e.g., blood, urine, etc.) conducted on the patient 19, and/or prior and/or current imaging of the patient 19 (e.g., Magnetic resonance imaging (MRI), Computed tomography scans (CAT), Positron emission tomography (PET), x-rays, ultra-sound, etc.). However, the present invention is not limited to such embodiments and more, fewer and/or other evaluation methods can be used to practice the invention.

Magnetic resonance imaging (MRI) is a medical imaging technique used in radiology to form pictures of the anatomy and the physiological processes inside the body. MRI scanners use strong magnetic fields, magnetic field gradients, and radio waves to generate images of the organs in the body. A computed tomography (CAT) scan is a medical imaging technique used to obtain detailed internal images of the body. Positron emission tomography (PET) is a functional imaging technique that uses radioactive substances known as radiotracers to visualize and measure changes in metabolic processes, and in other physiological activities including blood flow, regional chemical composition, and absorption. However, the present invention is not limited to such embodiments and more, fewer and/or other imaging methods can be used to practice the invention.

In one embodiment, morbidity is defined as a patient having a disease or a symptom of a disease. The morbidity threat level, includes, but is not limited to, an external cause of morbidity, that is, how an injury or health condition happened and/or its root cause (e.g., new condition, old chronic condition, etc.). Morbidity threat levels also include: (1) an intent: unintentional or accidental; or intentional, like suicide or assault or accident; and (2) a place where an event occurred; and/or (3) an activity of the patient at the time of the event. The actual morbidity threat level used include, but is not limited to, a minimum, low, moderate and high, morbidity threat level, as defined by the ICD. However, the present invention is not limited to such embodiments and more, fewer and/or other morbidity threat levels, with other levels and definitions can be used to practice the invention.

In FIG. 7C at Step 118, receiving a third message on the medical diagnosis application 30a on server network device 20, 22, 24, 26 including one or more selection inputs with differential diagnosis information selected for the one or more patient complaints 13 for the specific patient 19 at the medical facility 21 from the network device 12, 14, 16, 20, 22, 24, 26, 31, 33, 98-104 with via the communications network on the secure connection 23.

Figure 10:
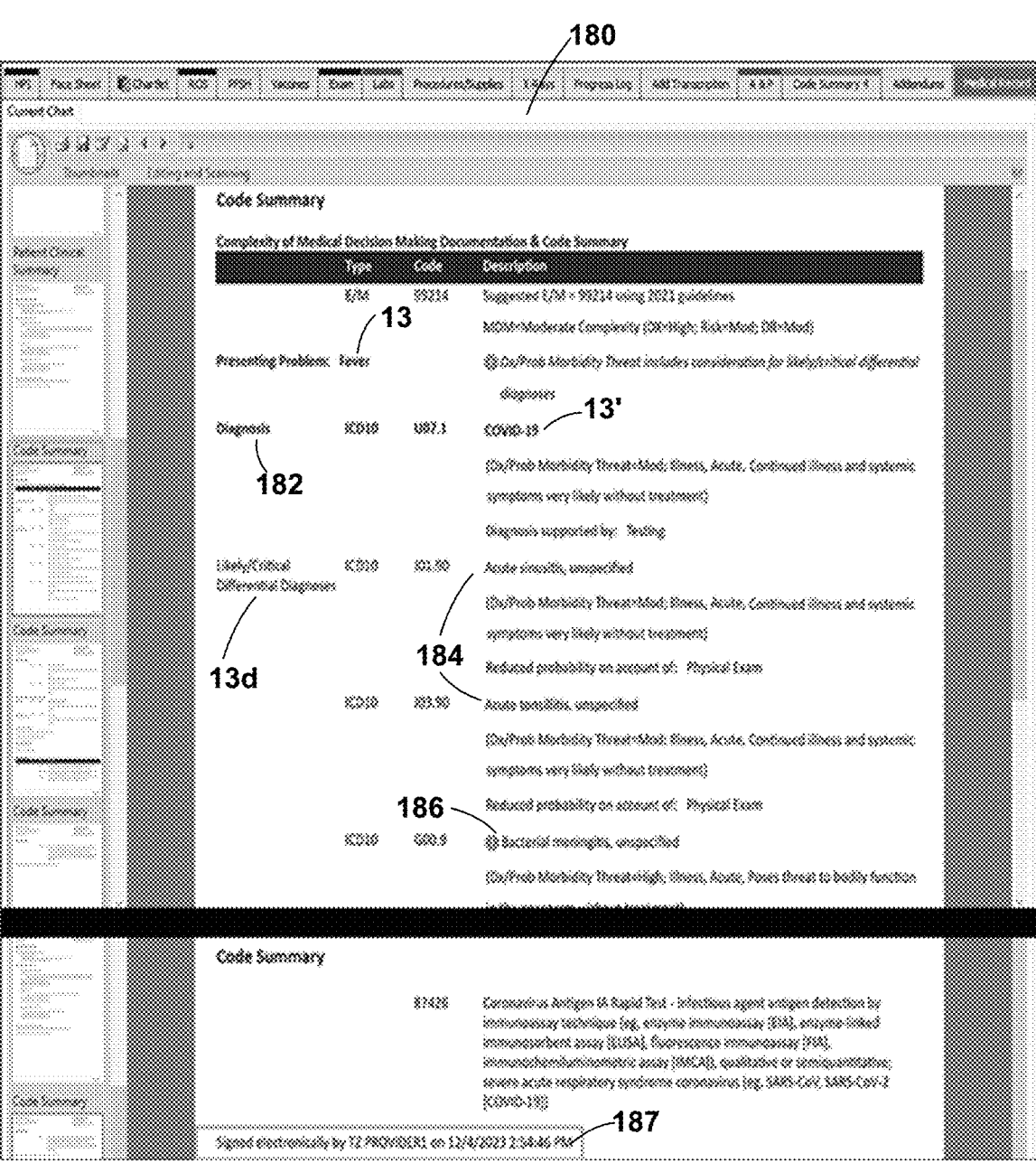
FIG. 10 is a block diagram illustrating an exemplary visit summary screen.

FIG. 10 is a block diagram 178 illustrating an exemplary visit summary screen 180.

FIG. 10 illustrates final diagnosis information 13' including a final diagnosis 182 (e.g., COVID 19, etc.) for the one or more patient complaints 13 (e.g., fever, etc.) for the specific patient 19 at the medical facility 21, and (2) differential diagnosis information 13d including one or more likely differential diagnoses 184 (acute sinusitis, acute tonsillitis, etc.) and one or more critical differential diagnoses 186 (e.g., bacterial meningitis, etc.) for the specific patient 19 at the medical facility 21. However, the present invention is not limited to such an embodiment and more, fewer and/or other fields can be used on the visit summary screen to practice the invention.

Returning to FIG. 7C at Step 120, determining on the medical diagnosis application 30a on server network device 20, 22, 24, 26, with one or more diagnosis methods with information from the first message, second message and third message; (1) final diagnosis information 13' including a final diagnosis 182 for the one or more patient complaints 13 for the specific patient 19 at the medical facility 21, and (2) differential diagnosis information 13d including one or more likely differential diagnoses 184 and one or more critical differential diagnoses 186 for the specific patient 19 at the medical facility 21. The created electronic visit summary 25, the created new medical record 27 and the created treatment plan 29 reducing a second complexity level and a second risk level associated with determining a final diagnosis 13', one or more differential diagnoses 13*d* related to the final diagnosis for the one or more patient complaints 13 for the specific patient 19 at the medical facility 21.

In one embodiment, the final diagnosis information 13' and the differential diagnosis information 13*d* are determined using one or more diagnosis methods include using the HX, CX, DX, PX and/or RISK information described in Table 4-7 above. However, the present invention is not limited to such an embodiment and other embodiments without using this information may be used to practice the invention.

In one embodiment, the final diagnosis information 13' and the differential diagnosis information 13*d* are determined using the one or more diagnosis methods without AI. In such an embodiment, the one or more diagnostic methods compare the one or more patient complaints 13 for the specific patient 19 at the medical facility 21 to plural diagnostic items and combinations thereof, including but not limited to, a using a current version of the ICD, a prior and/or current medical history of the patient 19, prior and/or current physical exam of the patent 19, prior and/or current diagnostic testing (e.g., blood, urine, etc.) conducted on the patient 19, and/or prior and/or current imaging of the patient 19 (e.g., Magnetic resonance imaging (MRI), Computed tomography scans (CAT), Positron emission tomography (PET), x-rays, ultra-sound, etc.), and/or one or more prior and/or current differential diagnoses for the patient 19. However, the present invention is not limited to such an embodiment and other embodiments including other diagnosis methods can be used to practice the invention.

In another embodiment, the final diagnosis information 13' and the differential diagnosis information 13*d* are determined using one or more diagnosis methods including, but not limited to, one or more AI methods 30*b* including a Big Data set 30*c*. In such an embodiment, the one or more AI methods 30*b* compares the one or more patient complaints 13 for the specific patient 19 at the medical facility 21 to plural diagnostic items and combinations thereof, including but not limited to, prior and current versions of the ICD, electronic versions of medical text books, electronic versions of medical disease references, online medical reference sources (e.g., Centers for Disease Control and Prevention (CDC), MEDSCAPE, MEDLINE, PUBMED, etc.) a prior and/or current medical history of the patient 19 and medical histories of similar patients (e.g., similar age, race, pre-existing conditions, medications, surgeries, etc.) in the Big Data set 30*c*, a prior and/or current physical exam of the patent 19, and/or physical exams of similar patients in the Big Data set 30*c*, prior and/or current diagnostic testing (e.g., blood, urine, etc.) conducted on the patient 19 and diagnostic testing for similar patients in the Big Data set 30*c* and/or prior and/or current imaging of the patient 19 (e.g., Magnetic resonance imaging (MRI), Computed tomography scans (CAT), Positron emission tomography (PET), x-rays, ultra-sound, etc.) and imaging for similar patients in the Big Data set 30*c*, one or more prior and/or current diagnoses and/or differential diagnoses for the patient 19 and prior current diagnoses and/or differential diagnoses for similar patients in the Big Data set 30*c*. However, the present invention is not limited to such an embodiment and other AI methods 30*b*, with more, fewer and/or other method items and/or with and/or without use of a Big Data set 30*c*, to determine the final diagnosis information 13' and the differential diagnosis information 13*d*. However, the present invention is not limited to such an embodiment and other embodiments including other AI diagnosis methods can be used to practice the invention.

In one embodiment, the medical diagnosis application 30*a* on server network device 20, 22, 24, 26 periodically (e.g., one a month, quarter, year, etc.) updates 137 (FIG. 8) the one or more diagnosis methods and the database 20', 22', 24', 26' to include new and/or updated disease diagnoses and/or differential diagnoses information. However, the present invention is not limited to such an embodiment and other embodiments including other AI diagnosis methods can be used to practice the invention.

Returning to FIG. 7C at Step 122, creating on the medical diagnosis application 30*a* on server network device 20, 22, 24, 24 with the one or more diagnosis methods with information from the first message, second message and third message (1) an electronic visit summary 25 (FIG. 1) for the specific patient 19 at the medical facility 21 supplied to the specific patent 19 at the medical facility 21 including the determined final diagnosis information 13' and differential diagnosis information 13*d*, (2) a new medical record 27 for the specific patient 19 at the medical facility 21 including the determined final diagnosis information 13' and differential diagnosis information 13*d*, and (3) a treatment plan 29 for the specific patent at the medical facility including the determined final diagnosis information and differential diagnosis information. The created electronic visit summary 25, the created new medical record 27 and the created treatment plan 29 reducing a second complexity level and a second risk level associated with determining a final diagnosis 13', one or more differential diagnoses 13*d* related to the final diagnosis 13' created for the one or more patient complaints 13 for the specific patient 19 at the medical facility 21.

The medical diagnosis application 30*a* on the server network device 20, 22, 24, 26 creates the final diagnosis information 13' including a final diagnosis 182 for the one or more patient complaints 13 for the specific patient 19 at the medical facility 21, differential diagnosis information 13*d* including one or more likely differential diagnoses 184 and one or more critical differential diagnoses 186, the created visit summary 25, the created medical record 27 and the created treatment plan 29 for the specific patient 19 at the medical facility 21 with the one or more diagnosis methods.

Therefore, a second complexity level and a second risk level are significantly reduced because a medical doctor 17 trying to determine a final diagnosis 13' and one or more differential diagnoses 13*d* for the specific patient 19 is presented with a comprehensive, integrated interface medical diagnosis application 30*a* that helps prevent the medical doctor 19 from missing and/or not considering important and relevant possible diagnoses and related possible differential diagnoses related to the one or more patient complaints 13 for the specific patient 19 and/or not considering and/or missing important and relevant possible actions for the specific patient 19, the created visit summary 25, the created medical record 27 and the created treatment plan 29 for the specific patient 19 at the medical facility 21.

In FIG. 7D at Step 124, storing from the medical diagnosis application 30*a* on server network device 20, 22, 24, 26 the determined final diagnosis information 13' and final differential diagnosis information 13*d*, the created electronic visit summary 25, the new medical record 27 and treatment plan 29 for the specific patent 19 at the medical facility 21 in the database 20', 22', 24', 26'.

In one embodiment, the determined final diagnosis information 13' and final differential diagnosis information 13*d*, electronic visit summary 25, the new medical record 27 and treatment plan 29 for the specific patent 19 at the medical facility 21 are stored in one or more cloud storage object 82 in a cloud database 20', 22', 24', 26' on a cloud communications network 18. However, the present invention is not limited to such an embodiment and other embodiments can be used to practice the invention with and/or without a cloud communications network 18.

At Step 126, displaying from the medical diagnosis application 30*a* on server network device, 20, 22, 24, 24, diagnosis summary information 13' related to the one on more patient complaints 13 for the specific patient 19 at medical facility 21 on the network device 12, 14, 16, 20, 22, 24, 26, 31, 33, 98-104 via the communication network 18, 18' on the secure connection 23. The diagnosis summary information 13' including: final diagnosis information including: (1) the final diagnosis 182 for the one or more patient complaints 13 for the specific patient 19 at the medical facility 21, (2) the differential diagnosis information 13*d* including one or more likely differential diagnoses 184 and critical differential diagnoses 186 for the specific patient 19 at the medical facility 21, (3) the created electronic visit summary 25 for the specific patient 19 at the medical facility 21 supplied to the specific patent 19 at the medical facility 21, (4) the created new medical record 27 for the specific patient 19 at the medical facility 19 and (5) the created treatment plan for the specific patient 19 supplied to the specific patent 19 at the medical facility 21.

Figure 11:
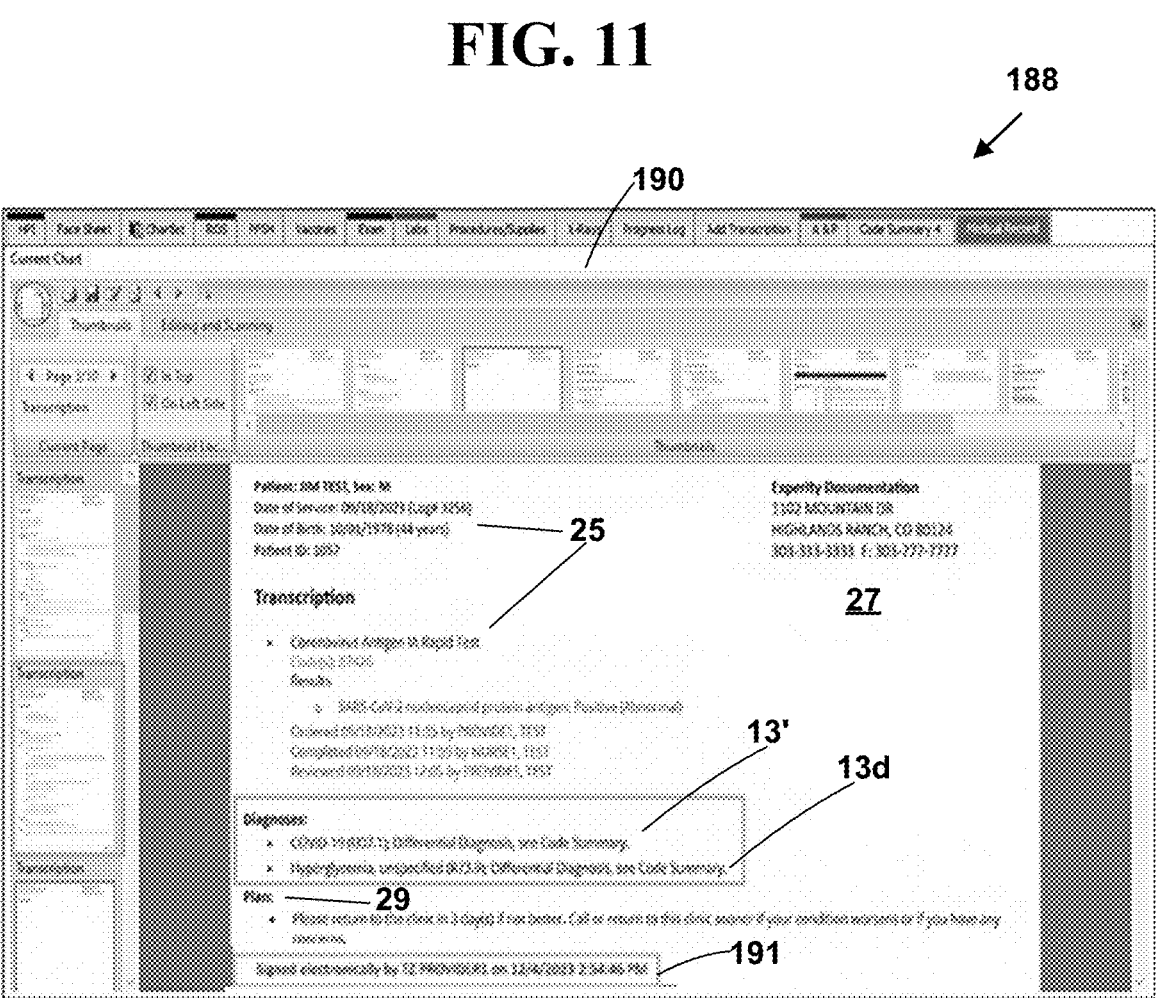
FIG. 11 is a block diagram illustrating an exemplary patient medical record.

FIG. 11 is a block diagram 188 illustrating an exemplary patient medical record screen 190.

FIG. 11 illustrates the created electronic visit summary 25, the created new medical record 27, and the created treatment plan 29 for the specific patient 19 at the medical facility 21 on one screen 190. However, the present invention is not limited to such an embodiment and other embodiments can be used to practice the invention.

Returning to FIG. 7D at step 128, sending a fourth message from the medical diagnosis application 30*a* on server network device 20, 22, 24, 26 to the server network device 12, 14, 16, 20, 22, 24, 26, 31, 33, 98-104 via the communication network 18, 18' on the secure connection 23. The fourth message including the created electronic visit summary 25, the created new medical record 27, and the created treatment plan 29 for the specific patient 19 at the medical facility 21.

In one embodiment, created electronic visit summary 25, the created new medical record 27, and the created treatment plan 29 for the specific patient 19 at the medical facility 21 are sent in one electronic document (as illustrated in FIG. 11) in the fourth message. In another embodiment, the created electronic visit summary 25, the created new medical record 27, and the created treatment plan 29 for the specific patient 19 at the medical facility 21 are sent in separate documents. However, the present invention is not limited to such embodiments and other embodiments can be used to practice the invention.

In one embodiment, adding from medical diagnosis application 30*a* on server network device an electronic signature 187 (FIG. 10), 191 (FIG. 11) for a medical professional (e.g., medical doctor 17, etc.) who reviewed: (1) the final diagnosis 182 for the one or more patient complaints 13 for the specific patient 19 at the medical facility 19, (2) the differential diagnosis information 13*d* including one or more likely differential diagnoses 184 and critical differential diagnoses 186 for the specific patient 19 at the medical facility 21, (3) the created electronic visit summary 25 for the specific patient 19 at the medical facility 21 supplied to the specific patent 19 at the medical facility 21, (4) the created new medical record 27 for the specific patient 19 at the medical facility 21 supplied to the specific patent 19 at the medical facility 21 and (5) the created treatment plan 29 for the specific patient 19. However, the present invention is not limited to such an embodiment and other embodiments with and/or without an electronic signature of a medical professional. The electronic signatures 187, 191 identifies the medical professional and prevents tampering and/or altering of the final diagnosis information 13' and differential diagnosis information 13*d*, the visit summary 25, new medical record 27 and treatment plan 29, after it is created.

Figure 12:
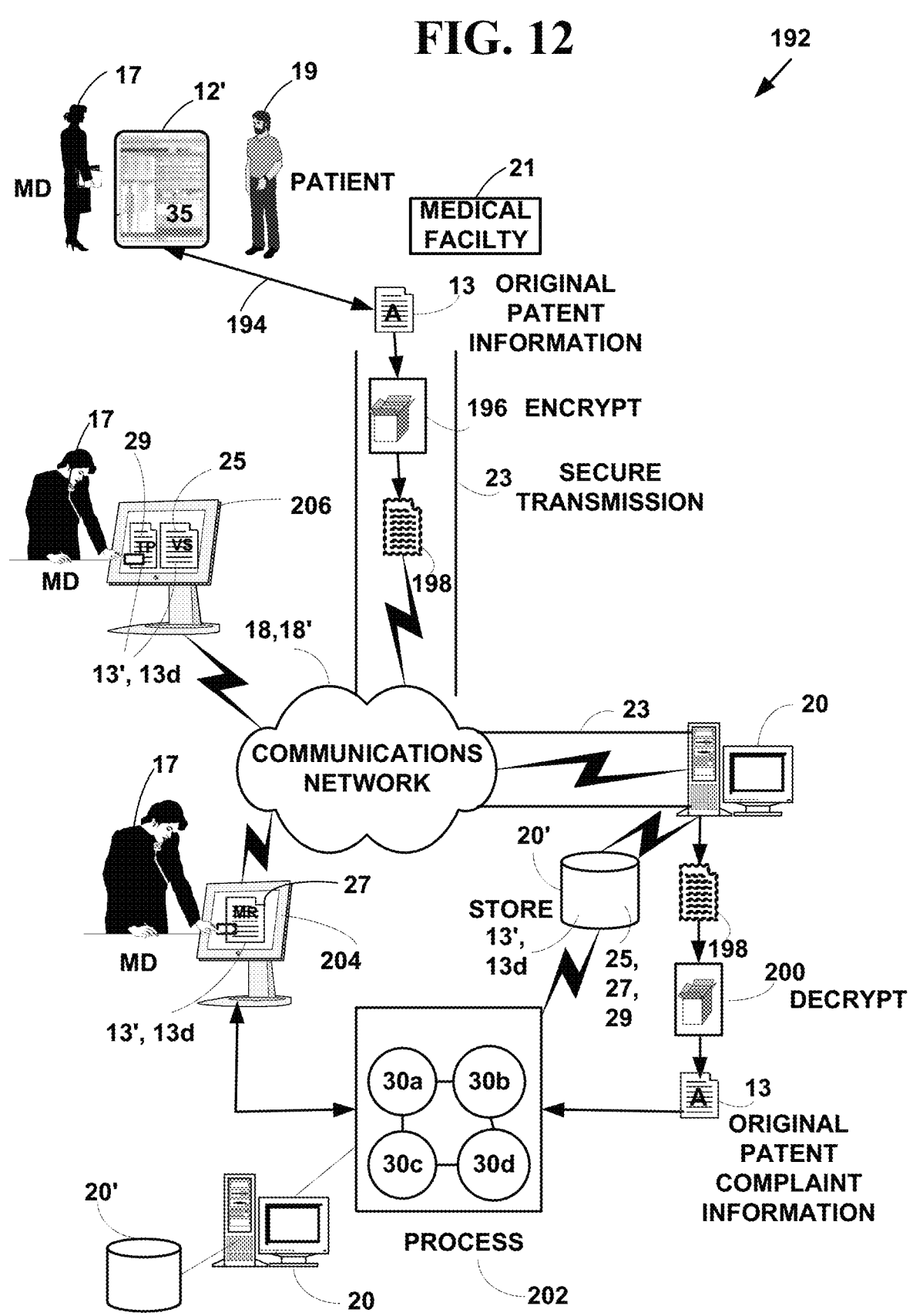
FIG. 12 is a block diagram illustrating an exemplary data flow for the method of FIG. 7.

FIG. 12 is a block diagram 192 illustrating an exemplary data flow 194 for the Method 106 of FIG. 7.

In FIG. 12, the one or more patient complaints 13 received for the patent 19 at a medical facility 21, are sent over the secure connection 23. The one or more patient complaints 13 are encrypted 196 with one or more encryption and/or security methods described herein to transform the one or more patient complaints 13 in their original plaintext format into an encrypted document 198 to protect the patent 19 data based on HIPAA security and encryption requirements. The medical diagnosis application 30*a* on server network device 20, 22, 24, 26 decrypts 200 the encrypted document 198 back into the original plaintext format 13. The medical doctor 17 uses the medical diagnosis application 30*a* on server network device 20, 22, 24, 26 to process 202 the one or more patient complaints 13 using Method 106 to create 204, 206 the final diagnosis information 13', the final differential diagnosis information 13*d*, the electronic visit summary 25, the new medical record 27 and the treatment plan 29 for the specific patent 19 at the medical facility 21. FIG. 12 illustrates the data flow 194 from the patent 19 to the medical doctor 17 using the medical diagnosis application 30*a* on server network device 20, 22, 24, 26 only. A data flow from the medical diagnosis application 30*a* on server network device 20, 22, 24, 26 back to a network device 12, 14, 16, 20, 22, 24, 26, 31, 33, 98-104 at the medical facility 21 or a network device 12, 14, 16, 20, 22, 24, 26, 31, 33, 98-104 accessible by the specific patent 19 (e.g., for telemedicine, etc.) would follow a similar pathway of encryption of plain text patent information 25, 27, 29 and description over the secure connection 23. However, the present invention is not limited to such an embodiment and other data flows can be used to practice the invention.

FIG. 13 is a flow diagram illustrating a Method 208 for providing automated differential medical diagnosis assessment.

In FIG. 13 at Step 210, determining on a medical diagnosis application on a server network device with one or more processors: (1) final diagnosis information including a final diagnosis for one or more patient complaints for a specific patient at a medical facility, (2) differential diagnosis information including one or more likely differential diagnoses and one or more critical differential diagnoses associated with the final diagnosis for the specific patient at the medical facility and (3) a treatment plan or the specific patient at the medical facility. At Step 212, reducing plural complexities and plural risks associated with determining the final diagnosis, the one or more differential diagnoses, the one or more critical diagnosis associated with the final diagnosis and the treatment plan for the one or more patient complaints for the specific patient at the medical facility.

Method 208 is illustrated with an exemplary embodiment. However, the present invention is not limited to such an embodiment and other embodiments may be used to practice the invention.

In such an exemplary embodiment in FIG. 13 at Step 210, determining on a medical diagnosis application 30a on server network device 20, 22, 24, 26 with one or more processors: (1) final diagnosis information 13' including a final diagnosis 182 for one or more patient complaints 13 for the specific patient 19 at the medical facility 21, (2) differential diagnosis information 13d including one or more likely differential diagnoses 184 and one or more critical differential diagnoses 186 associated with the final diagnosis 184 for the specific patient 19 at the medical facility 21 and (3) a treatment plan 29 for the specific patient 19 at the medical facility 21.

At Step 212, reducing plural complexities and plural risks associated with determining the final diagnosis 182, one or more differential diagnoses 184 and one or more critical diagnoses 186 associated with the final diagnosis 182 and the treatment plan 29 for the one or more patient complaints 13 for the specific patient 19 at the medical facility 21.

With Method 208, a first and second complexity level and a first and second risk level are significantly reduced because a medical doctor 17 trying to determine a final diagnosis and one or more differential diagnoses for the specific patient 19 is presented with a comprehensive, integrated interface that helps prevent the medical doctor 19 from missing and/or not considering important and relevant possible diagnoses and related possible differential diagnoses related to the one or more patient complaints 13 for the specific patient 19 and/or not considering and/or missing important and relevant possible actions for the specific patient 19 treatment plan 29.

FIG. 14 is a flow diagram illustrating a Method 214 for providing automated differential medical diagnosis assessment.

In FIG. 14 at Step 216, determining on a medical diagnosis application on server network device differential diagnosis information including one or more likely differential diagnoses and one or more critical differential diagnoses associated including determining plural morbidity threat levels for the one or more likely differential diagnoses and the one or more critical differential diagnoses for the specific patient at the medical facility. At Step 218, reducing plural complexities and plural risks associated with the determined one or more differential diagnoses and the determined one or more critical diagnoses for the specific patient at the medical facility with the determined plural morbidity threat levels for the specific patient at the medical facility.

Method 214 is illustrated with an exemplary embodiment. However, the present invention is not limited to such an embodiment and other embodiments may be used to practice the invention.

In such an exemplary embodiment in FIG. 14 at Step 216, determining on a medical diagnosis application 30a on server network device 20, 22, 24, 26, differential diagnosis information 13d including one or more likely differential diagnoses 184 and one or more critical differential diagnoses 186 associated including determining plural morbidity threat levels 174 for the one or more likely differential diagnoses 184 and the one or more critical differential diagnoses 186 for the specific patient 19 at the medical facility 21.

At Step 218, reducing plural complexities and plural risks associated with the determined one or more differential diagnoses 184 and the determined one or more critical diagnoses 186 for the specific patient 19 at the medical facility 21 with the determined plural morbidity threat levels 174 for the specific patient 19 at the medical facility 21.

With Method 214, a first and second complexity level and a first and second risk level are significantly reduced because a medical doctor 17 trying to determine a final diagnosis and one or more differential diagnoses for the specific patient 19 is presented with a comprehensive, integrated interface via the medical diagnosis application 30a that helps prevent the medical doctor 19 from missing and/or not considering important and relevant possible diagnoses and related possible differential diagnoses related to the one or more patient complaints 13 for the specific patient 19 and/or not considering and/or missing important and relevant possible actions for the specific patient 19 treatment plan 29.

With Method 214, third complexity level and a third risk level is significantly reduced because a medical doctor 17 trying to determine a diagnosis for the specific patient 19 is presented with a comprehensive, integrated interface via the medical diagnosis application 30a that helps prevent the medical doctor 19 from missing and/or not considering important and relevant plural morbidity threat levels 174 for the one or more likely differential diagnoses 184 and the one or more critical differential diagnoses 186 for the specific patient 19 at the medical facility related to the one or more patient complaints 13 for the specific patient 19.

All of the drawings included here do not include any actual data for any actual patents and not violate the Health Insurance Portability and Accountability Act (HIPAA) rules that protect the privacy of patent information. FIGS. 8-11 are included for illustrative purposes for virtual patient that is not a real person.

A method and system for automated differential medical diagnosis is presented herein. Final diagnosis information including a final diagnosis for one or more patient complaints for a specific patient at a medical facility and differential diagnosis information including one or more likely differential diagnoses and one or more critical differential diagnoses associated with the final diagnosis for the specific patient at the medical facility, a visit summary, a medical record and a treatment plan or the specific patient at the medical facility are determined. Plural different types of complexities and plural types of risks associated with determining the final diagnosis, the one or more differential diagnoses, the one or more critical diagnosis associated with the final diagnosis, the visit summary, the medical record and the treatment plan for the one or more patient complaints for the specific patient at the medical facility are reduced.

It should be understood that the architecture, programs, processes, methods and systems described herein are not related or limited to any particular type of computer or network system (hardware or software), unless indicated otherwise. Various types of specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

While various elements of the preferred embodiments have been described as being implemented in software, in other embodiments hardware or firmware implementations may alternatively be used, and vice-versa.

The claims should not be read as limited to the described order or elements unless stated to that effect. In addition, use of the term "means" in any claim is intended to invoke 35 U.S.C. § 112, paragraph 6, and any claim without the word "means" is not so intended. Therefore, all embodiments that come within the scope and spirit of the following claims and equivalents thereto are claimed as the invention.

Therefore, all embodiments that come within the scope and spirit of the proceeding described and equivalents thereto are identified and claimed as the invention.

I claim:

1. A method for providing automated differential medical diagnosis, comprising:

providing a medical diagnosis application as a Software as a Service (Saas) on a cloud server network device with one or more processors via a cloud communications network, the SaaS medical diagnosis application including a comprehensive, integrated, graphical user interface (GUI) with a plurality of different differential diagnosis display screens that reduces a risk level and a complexity level three ways: (1) reducing a first risk level and a first complexity level by providing a list of a possible diagnoses and a list of related possible differential diagnoses related to one or more patient complaints obtained for a specific patient at a medical facility, (2) reducing a second risk level and a second complexity level associated with determining a final diagnosis related to the one or more patient complaints obtained for the specific patient at the medical facility by providing a created electronic visit summary, a created new medical record and a created treatment plan, related to one or more patient complaints obtained for the specific patient at the medical facility, and (3) reducing a third risk level and a third complexity level by providing a list of a plurality of morbidity threat levels for medical diagnoses related to one or more patient complaints obtained for the specific patient at the medical facility;

displaying from the (SaaS) medical diagnosis application on the cloud server network device with one or more processors, a list of a plurality of patient complaints from the one or more cloud databases for one or more patient complaints received at the a medical facility, on a network device with one or more processors via the cloud communications network on a secure connection, the one or more cloud databases including one or more cloud storage objects comprising one or more of a REpresentational State Transfer (REST), Simple Object Access Protocol (SOAP) or Lightweight Directory Access Protocol (LDAP) cloud storage objects, portions thereof, or combinations thereof, stored in the one or more cloud databases;

receiving a first message on the SaaS medical diagnosis application on the cloud server network device including the one or more patient complaints for a specific patient at the medical facility from the network device with via the cloud communications network on the secure connection;

displaying from the SaaS medical diagnosis application on the cloud server network device, a list of a possible differential diagnoses related to the one or more patient complaints for the specific patient on the graphical user interface (GUI) with the plurality of different differential diagnosis display screens on the network device via the cloud communications network on the secure connection, the first differential diagnosis display screen on the GUI including:

the list of possible differential diagnoses related to the one or more patient complaints including: (1) a graphical check box to include differential diagnoses for the one or more patient complaints including a differential name and differential diagnosis description, (2) a diagnosis code (Dx), (3) a delete diagnosis icon to remove a diagnosis that does not apply to the specific patient from the list, and (4) an add diagnosis link including a link to a list of additional related diagnoses that could apply to the specific patient including one or more electronic links to add additional diagnoses to the list of a plurality of patient complaints displayed for the one or more patient complaints received in the first message, and the first differential diagnosis display screen on the GUI including the plurality of sections with the list of possible differential diagnoses reducing a first complexity level and a first risk level associated with determining a primary diagnosis and one or more differential diagnoses related to the one or more patient complaints for the specific patient at the medical facility;

receiving a second message on the SaaS medical diagnosis application on the cloud server network device including one or more selection inputs with diagnosis information selected for the one or more patient complaints for the specific patient at the medical facility from the network device with via the cloud communications network on the secure connection;

displaying from the SaaS medical diagnosis application on the cloud server network device, diagnosis information and differential diagnosis information related to the one or more patient complaints for the specific patient on a second differential diagnosis display screen with a second plurality of sections on the GUI on the network device via the cloud communications network on the secure connection;

the second differential diagnosis display screen with the second plurality of sections on the GUI comprising:

the diagnosis information and differential diagnosis information including: (1) a determined diagnosis section including a graphical checkbox to add the determined diagnosis as a final diagnosis for the one or more patient complaints for the specific patient at the medical facility, (2) a differential diagnosis section including a graphical checkbox to add one or more differential diagnoses for the specific patient at the medical facility, (3) a diagnosis name section including a diagnosis description and an International Classification of Diseases (ICD) diagnostic code, (4) a list of evaluation methods section used to include and rule out one or more differential diagnoses and select a final diagnosis, (5) a diagnosis (Dx) morbidity threat section including a list of plurality of morbidity threat levels for the one or more differential diagnoses, and (6) a search section including a graphical search electronic link to search for additional diagnoses to add to the likely differential diagnosis list;

receiving a third message on the SaaS medical diagnosis application on the cloud server network device including one or more selection inputs with differential diagnosis information selected for the one or more patient complaints for the specific patient at the medical facility from the network device with via the cloud communications network on the secure connection;

determining automatically on the SaaS medical diagnosis application on the cloud server network device with the one or more medical diagnosis methods with information from the first message, second message and third messages: (1) final diagnosis information including a final diagnosis for the one or more patient complaints for the specific patient at the medical facility, and (2) differential diagnosis information including one or more likely differential diagnoses and one or more critical differential diagnoses for the specific patient at the medical facility;

creating automatically on the SaaS medical diagnosis application on the cloud server network device with the one or more diagnosis methods with information from the first message, second message and third messages: (1) an electronic visit summary for the specific patient at the medical facility supplied to the specific patient at the medical facility including the determined final diagnosis information and differential diagnosis information, (2) a new medical record for the specific patient at the medical facility including the determined final diagnosis information and differential diagnosis information, and (3) a treatment plan for the specific patient at the medical facility including the determined final diagnosis information and differential diagnosis information, the created electronic visit summary, the created new medical record and the created treatment plan reducing a second complexity level and a second risk level associated with determining a final diagnosis, one or more differential diagnoses created for the one or more patient complaints for the specific patient at the medical facility;

determining automatically on the SaaS medical diagnosis application on cloud server network device a plurality of morbidity threat levels for the determined final diagnosis information, the determined differential diagnosis information including the one or more likely differential diagnoses and the determined one or more critical differential diagnoses for the specific patient at the medical facility, the determined plurality of morbidity threat levels reducing a third complexity level and a third risk level associated with diagnosing medical problems for the one or more patient complaints for the specific patient at the medical facility;

storing from the SaaS medical diagnosis application on the cloud server network device the determined final diagnosis information and differential diagnosis information, the determined electronic visit summary, the created new medical record and the created treatment plan for the specific patient at the medical facility in the one or more cloud databases, including the one or more cloud storage objects comprising the one or more of the REpresentational State Transfer (REST), Simple Object Access Protocol (SOAP) or Lightweight Directory Access Protocol (LDAP) cloud storage objects, portions thereof, or combinations thereof, stored in the one or more cloud databases;

displaying from the SaaS medical diagnosis application on the cloud server network device, diagnosis summary information related to the one on more patient complaints for the specific patient at medical facility on a third differential diagnosis display screen with a third plurality of sections on the GUI on the network device via the cloud communications network on the secure connection;

the diagnosis summary information including: final diagnosis information including: (1) the final diagnosis for the one or more patient complaints for the specific patient at the medical facility, (2) the differential diagnosis information including one or more likely differential diagnoses and critical differential diagnoses for the specific patient at the medical facility, (3) the created electronic visit summary for the specific patient at the medical facility supplied to the specific patient at the medical facility, (4) the created new medical record for the specific patient at the medical facility supplied to the specific patient at the medical facility (5) the created treatment plan for the specific patient; and sending a fourth message from the from the SaaS medical diagnosis application on the cloud server network device to the network device via the cloud communications network on the secure connection, the fourth message including the created new medical record, the created electronic visit summary and the created treatment plan for the specific patient at the medical facility.

2. The method of claim 1 wherein, the SaaS medical diagnosis application on the cloud server network device further includes an Artificial intelligence (AI) application with a Big Data set.

3. The method of claim 1 wherein, the one or more medical diagnosis methods include one or more artificial intelligence (AI) methods with a Big Data set.

4. The method of claim 3 wherein, the one or more AI methods with a Big Data set include:

comparing the one or more patient complaints for the specific patient at the medical facility to a plurality of diagnostic items and combinations thereof, including: current versions of the International Classification of Diseases (ICD), electronic versions of medical text books, electronic versions of medical disease references, online medical reference sources, a prior or current medical history of the patient and medical histories of similar patients in the Big Data set, a prior or current physical exam of the patient and physical exams of similar patients in the Big Data set, a prior or current diagnostic testing conducted on the patient and diagnostic testing for similar patients in the Big Data set, a prior or current imaging of the patient and imaging for similar patients in the Big Data set, one or more prior or current diagnoses or differential diagnoses for the patient and prior current diagnoses or differential diagnoses for similar patients with similar patient complaints in the Big Data set; and determining with the with the comparison of the plurality of diagnostic items, the final diagnosis information including the final diagnosis for the one or more patient complaints for the specific patient at the medical facility and differential diagnosis information including one or more likely differential diagnoses and one or more critical differential diagnoses for the specific patient at the medical facility.

5. The method of claim 1 wherein, the one or more diagnosis methods include:

comparing the one or more patient complaints for the specific patient at the medical facility to a plurality of diagnostic items and combinations thereof, including: current versions of the International Classification of Diseases (ICD), electronic versions of medical text books, electronic versions of medical disease references, online medical reference sources, a prior or current medical history of the patient, a prior or current physical exam of the patient, a prior or current diagnostic testing conducted on the patient, a prior or current imaging of the patient and, one or more prior or current diagnoses or differential diagnoses for the patient; and determining with the with the comparison of the plurality of diagnostic items, the final diagnosis information including the final diagnosis for the one or more patient complaints for the specific patient at the medical facility and differential diagnosis information including one or more likely differential diagnoses and one or more critical differential diagnoses for the specific patient at the medical facility.

6. The method of claim 1 wherein, the list of evaluation methods used to rule out a likely differential diagnosis or select a final diagnosis includes, considering a patient history, a physical exam of the patient, medical testing on the patient and imaging conducted on the patient.

7. The method of claim 6 wherein, the imaging conducted on the patient include one or more of: magnetic resonance imaging (MRI), computed tomography scans (CAT), positron emission tomography (PET), x-ray, or ultra-sound, imaging.

8. The method of claim 1 wherein, the diagnosis (Dx) morbidity threat section including the list of plurality of morbidity threat levels for the diagnosis comprises: a minimal, low, moderate and high, morbidity threat level.

9. The method of claim 1, wherein the diagnosis (Dx) morbidity threat including the plurality of morbidity threat levels for the diagnosis also further reduces the third complexity level and the third risk level associated with determining the final diagnosis, one or more differential diagnoses related to the final diagnosis and the created treatment plan created for the one or more patient complaints for the specific patient with the plurality of morbidity threat levels by including a list of minimal, low, moderate and high, morbidity threat levels for the one or more patient complaints for the specific patient.

10. The method of claim 1 wherein, the network device and the server network device include one or more wireless communications interfaces comprising: cellular telephone, 802.11a, 802.11b, 802.11g, 802.11n, 802.15.4 (ZigBee), Wireless Fidelity (Wi-Fi), Wi-Fi Aware, Worldwide Interoperability for Microwave Access (WiMAX), ETSI High Performance Radio Metropolitan Area Network (HIPERMAN), Near Field Communications (NFC), Machine-to-Machine (M2M), 802.15.1 (BLUETOOTH), or infra data association (IrDA), wireless communication interfaces.

11. The method of claim 1 wherein, the network device includes: server network devices, desktop computers, laptop computers, tablet computers, mobile phones, smart phones, personal digital/data assistants (PDA), wearable network devices, Internet of Things (IoT) devices, cable television (CATV) set-top boxes, satellite television boxes, or digital televisions including high-definition (HDTV) or three-dimensional (3D) televisions.

12. The method of claim 1 wherein, the messages include: an email message, Rich Communications Suite (RCS) message, Short Message Service (SMS) message, Multimedia Messaging Service (MMS) message, instant message, direct message, Short Message Peer-to-Peer (SMPP) message, or REpresentational State Transfer (REST) message.

13. The method of claim 1, further comprising:
updating periodically from the SaaS medical diagnosis application on the cloud server network device the one or more diagnosis methods and the one or more cloud databases to include new and updated disease diagnoses and differential diagnoses information via the cloud communications network.

14. The method of claim 1, further comprising:
adding from the SaaS medical diagnosis application on the cloud server network device an electronic signature for a medical professional who reviewed:
(1) the final diagnosis for the one or more patient complaints for the specific patient at the medical facility, (2) the differential diagnosis information including one or more likely differential diagnoses and critical differential diagnoses for the specific patient at the medical facility, (3) the created electronic visit summary for the specific patient at the medical facility supplied to the specific patient at the medical facility, (4) the created new medical record for the specific patient at the medical facility supplied to the specific patient at the medical facility and (5) the created treatment plan for the specific patient.

15. The method of claim 1 wherein, the secure connection includes using: Wireless Encryption Protocol (WEP), Advanced Encryption Standard (AES), Data Encryption Standard (DES), RSA encryption, Secure Hash Algorithm (SHA), Message Digest-5 (MD-5), Keyed Hashing for Message Authentication Codes (HMAC), Electronic Code Book (ECB), Diffie and Hellman (DH) or Secure Sockets Layer (SSL), security methods, on the secure connection.

16. The method of claim 1 wherein, the electronic links include: a Uniform Resource Locator (URL), Hyper Text Transfer Protocol (HTTP), Hyper Text Transfer Protocol Secure (HTTPS), cloud REpresentational State Transfer (REST), Application Program Interface (API), Short Message Peer-to-Peer (SMPP), operating system call, deep link, mobile deep link, or deferred deep link, electronic links.

17. The method of claim 1 wherein, the cloud server network device includes a plurality of cloud applications and the one or more cloud databases communicating with the cloud communications network, the plurality of cloud applications providing a plurality of automated differential medical diagnosis cloud services including: a cloud computing Infrastructure as a Service (IaaS), a cloud computing Platform as a Service (PaaS) and the automated differential medical diagnosis application as the Software as a Service (Saas).

18. The method of claim 1 wherein, the messages include Rich Communications Suite (RCS) messages comprising: person-to-person (P2P), application-to-person (A2P), application-to-application (A2A), application-to-device (A2D) or device-to-device (D2D) messaging.

19. One or more non-transitory computer readable mediums each having stored therein a plurality of instructions for causing one or more processors, on one more network devices, to execute the steps of:
providing a medical diagnosis application as a Software as a Service (Saas) on a cloud server network device with one or more processors via a cloud communications network,
the SaaS medical diagnosis application including a comprehensive, integrated, graphical user interface (GUI) with a plurality of different differential diagnosis display screens that reduces a risk level and a complexity level three ways: (1) reducing a first risk level and a first complexity level by providing a list of a possible diagnoses and a list of related possible differential diagnoses related to one or more patient complaints obtained for a specific patient at a medical facility, (2) reducing a second risk level and a second complexity level associated with determining a final diagnosis related to the one or more patient complaints obtained for the specific patient at the medical facility by providing a created electronic visit summary, a created new medical record and a created treatment plan, related to one or more patient complaints obtained for the specific patient at the medical facility, and (3) reducing a third risk level and a third complexity level by providing a list of a plurality of morbidity threat levels for medical diagnoses related to one or more patient complaints obtained for the specific patient at the medical facility;

displaying from the (SaaS) medical diagnosis application on the cloud server network device with one or more processors, a list of a plurality of patient complaints from the one or more cloud databases for one or more patient complaints received at the medical facility, on a network device with one or more processors via the cloud communications network on a secure connection, the one or more cloud databases including one or more cloud storage objects comprising one or more of a REpresentational State Transfer (REST), Simple Object Access Protocol (SOAP) or Lightweight Directory Access Protocol (LDAP) cloud storage objects, portions thereof, or combinations thereof, stored in the one or more cloud databases;

receiving a first message on the SaaS medical diagnosis application on the cloud server network device including the one or more patient complaints for a specific patient at the medical facility from the network device with via the cloud communications network on the secure connection;

displaying from the SaaS medical diagnosis application on the cloud server network device, a list of a possible differential diagnoses related to the one or more patient complaints for the specific patient on the graphical user interface (GUI) with the plurality of different differential diagnosis display screens on the network device via the cloud communications network on the secure connection, the first differential diagnosis display screen on the GUI including:

the list of possible differential diagnoses related to the one or more patient complaints including: (1) a graphical check box to include differential diagnoses for the one or more patient complaints including a differential name and differential diagnosis description, (2) a diagnosis code (Dx), (3) a delete diagnosis icon to remove a diagnosis that does not apply to the specific patient from the list, and (4) an add diagnosis link including a link to a list of additional related diagnoses that could apply to the specific patient including one or more electronic links to add additional diagnoses to the list of a plurality of patient complaints displayed for the one or more patient complaints received in the first message, and the first differential diagnosis display screen on the GUI including the plurality of sections with the list of possible differential diagnoses reducing a first complexity level and a first risk level associated with determining a primary diagnosis and one or more differential diagnoses related to the one or more patient complaints for the specific patient at the medical facility;

receiving a second message on the SaaS medical diagnosis application on the cloud server network device including one or more selection inputs with diagnosis information selected for the one or more patient complaints for the specific patient at the medical facility from the network device with via the cloud communications network on the secure connection;

displaying from the SaaS medical diagnosis application on the cloud server network device, diagnosis information and differential diagnosis information related to the one or more patient complaints for the specific patient on a second differential diagnosis display screen with a second plurality of sections on the GUI on the network device via the cloud communications network on the secure connection;

the second differential diagnosis display screen with the second plurality of sections on the GUI comprising:

the diagnosis information and differential diagnosis information including: (1) a determined diagnosis section including a graphical checkbox to add the determined diagnosis as a final diagnosis for the one or more patient complaints for the specific patient at the medical facility, (2) a differential diagnosis section including a graphical checkbox to add one or more differential diagnoses for the specific patient at the medical facility, (3) a diagnosis name section including a diagnosis description and an International Classification of Diseases (ICD) diagnostic code, (4) a list of evaluation methods section used to include and rule out one or more differential diagnoses and select a final diagnosis, (5) a diagnosis (Dx) morbidity threat section including a list of plurality of morbidity threat levels for the one or more differential diagnoses, and (6) a search section including a graphical search electronic link to search for additional diagnoses to add to the likely differential diagnosis list;

receiving a third message on the SaaS medical diagnosis application on the cloud server network device including one or more selection inputs with differential diagnosis information selected for the one or more patient complaints for the specific patient at the medical facility from the network device with via the cloud communications network on the secure connection;

determining automatically on the SaaS medical diagnosis application on the cloud server network device with the one or more medical diagnosis methods with information from the first message, second message and third messages: (1) final diagnosis information including a final diagnosis for the one or more patient complaints for the specific patient at the medical facility, and (2) differential diagnosis information including one or more likely differential diagnoses and one or more critical differential diagnoses for the specific patient at the medical facility;

creating automatically on the SaaS medical diagnosis application on the cloud server network device with the one or more diagnosis methods with information from the first message, second message and third messages: (1) an electronic visit summary for the specific patient at the medical facility supplied to the specific patient at the medical facility including the determined final diagnosis information and differential diagnosis information, (2) a new medical record for the specific patient at the medical facility including the determined final diagnosis information and differential diagnosis information, and (3) a treatment plan for the specific patient at the medical facility including the determined final diagnosis information and differential diagnosis information, the created electronic visit summary, the created new medical record and the created treatment plan reducing a second complexity level and a second risk level associated with determining a final diagnosis, one or more differential diagnoses created for the one or more patient complaints for the specific patient at the medical facility;

determining automatically on the SaaS medical diagnosis application on cloud server network device a plurality of morbidity threat levels for the determined final diagnosis information, the determined differential diagnosis information including the one or more likely differential diagnoses and the determined one or more critical differential diagnoses for the specific patient at the medical facility, the determined plurality of morbidity threat levels reducing a third complexity level and a third risk level associated with diagnosing medical problems for the one or more patient complaints for the specific patient at the medical facility;

storing from the SaaS medical diagnosis application on the cloud server network device the determined final diagnosis information and differential diagnosis information, the determined electronic visit summary, the created new medical record and the created treatment plan for the specific patient at the medical facility in the one or more cloud databases, including the one or more cloud storage objects comprising the one or more of the REpresentational State Transfer (REST), Simple Object Access Protocol (SOAP) or Lightweight Directory Access Protocol (LDAP) cloud storage objects, portions thereof, or combinations thereof, stored in the one or more cloud databases;

displaying from the SaaS medical diagnosis application on the cloud server network device, diagnosis summary information related to the one on more patient complaints for the specific patient at medical facility on a third differential diagnosis display screen with a third plurality of sections on the GUI on the network device via the cloud communications network on the secure connection;

the diagnosis summary information including: final diagnosis information including: (1) the final diagnosis for the one or more patient complaints for the specific patient at the medical facility, (2) the differential diagnosis information including one or more likely differential diagnoses and critical differential diagnoses for the specific patient at the medical facility, (3) the created electronic visit summary for the specific patient at the medical facility supplied to the specific patient at the medical facility, (4) the created new medical record for the specific patient at the medical facility supplied to the specific patient at the medical facility (5) the created treatment plan for the specific patient; and sending a fourth message from the from the SaaS medical diagnosis application on the cloud server network device to the network device via the cloud communications network on the secure connection, the fourth message including the created new medical record, the created electronic visit summary and the created treatment plan for the specific patient at the medical facility.

20. A system for automated differential medical diagnosis, comprising in combination:

one or more network devices, each with one or more processors;

one or more cloud server network devices, each with one or more processors;

a cloud communications network;

the one or more processors on the one or more network devices and one or more cloud server network devices including a plurality of instructions configured:

for providing a medical diagnosis application as a Software as a Service (SaaS) on a cloud server network device with one or more processors via the cloud communications network, the SaaS medical diagnosis application including a comprehensive, integrated, graphical user interface (GUI) with a plurality of different differential diagnosis display screens that reduces a risk level and a complexity level three ways: (1) reducing a first risk level and a first complexity level by providing a list of a possible diagnoses and a list of related possible differential diagnoses related to one or more patient complaints obtained for a specific patient at a medical facility, (2) reducing a second risk level and a second complexity level associated with determining a final diagnosis related to the one or more patient complaints obtained for the specific patient at the medical facility by providing a created electronic visit summary, a created new medical record and a created treatment plan, related to one or more patient complaints obtained for the specific patient at the medical facility, and (3) reducing a third risk level and a third complexity level by providing a list of a plurality of morbidity threat levels for medical diagnoses related to one or more patient complaints obtained for the specific patient at the medical facility;

for displaying from the (SaaS) medical diagnosis application on the cloud server network device with one or more processors, a list of a plurality of patient complaints from the one or more cloud databases for one or more patient complaints received at the medical facility, on a network device with one or more processors via the cloud communications network on a secure connection, the one or more cloud databases including one or more cloud storage objects comprising one or more of a REpresentational State Transfer (REST), Simple Object Access Protocol (SOAP) or Lightweight Directory Access Protocol (LDAP) cloud storage objects, portions thereof, or combinations thereof, stored in the one or more cloud databases;

for receiving a first message on the SaaS medical diagnosis application on the cloud server network device including the one or more patient complaints for a specific patient at the medical facility from the network device with via the cloud communications network on the secure connection;

for displaying from the SaaS medical diagnosis application on the cloud server network device, a list of a possible differential diagnoses related to the one or more patient complaints for the specific patient on the graphical user interface (GUI) with the plurality of different differential diagnosis display screens on the network device via the cloud communications network on the secure connection, the first differential diagnosis display screen on the GUI including:

the list of possible differential diagnoses related to the one or more patient complaints including: (1) a graphical check box to include differential diagnoses for the one or more patient complaints including a differential name and differential diagnosis description, (2) a diagnosis code (Dx), (3) a delete diagnosis icon to remove a diagnosis that does not apply to the specific patient from the list, and (4) an add diagnosis link including a link to a list of additional related diagnoses that could apply to the specific patient including one or more electronic links to add additional diagnoses to the list of a plurality of patient complaints displayed for the one or more patient complaints received in the first message, and the first differential diagnosis display screen on the GUI including the plurality of sections with the list of possible differential diagnoses reducing a first complexity level and a first risk level associated with determining a primary diagnosis and one or more differential diagnoses related to the one or more patient complaints for the specific patient at the medical facility;

for receiving a second message on the SaaS medical diagnosis application on the cloud server network device including one or more selection inputs with diagnosis information selected for the one or more patient complaints for the specific patient at the medical facility from the network device with via the cloud communications network on the secure connection;

for displaying from the SaaS medical diagnosis application on the cloud server network device, diagnosis information and differential diagnosis information related to the one or more patient complaints for the specific patient on a second differential diagnosis display screen with a second plurality of sections on the GUI on the network device via the cloud communications network on the secure connection;

the second differential diagnosis display screen with the second plurality of sections on the GUI comprising:

the diagnosis information and differential diagnosis information including: (1) a determined diagnosis section including a graphical checkbox to add the determined diagnosis as a final diagnosis for the one or more patient complaints for the specific patient at the medical facility, (2) a differential diagnosis section including a graphical checkbox to add one or more differential diagnoses for the specific patient at the medical facility, (3) a diagnosis name section including a diagnosis description and an International Classification of Diseases (ICD) diagnostic code, (4) a list of evaluation methods section used to include and rule out one or more differential diagnoses and select a final diagnosis, (5) a diagnosis (Dx) morbidity threat section including a list of plurality of morbidity threat levels for the one or more differential diagnoses, and (6) a search section including a graphical search electronic link to search for additional diagnoses to add to the likely differential diagnosis list;

for receiving a third message on the SaaS medical diagnosis application on the cloud server network device including one or more selection inputs with differential diagnosis information selected for the one or more patient complaints for the specific patient at the medical facility from the network device with via the cloud communications network on the secure connection;

for determining automatically on the SaaS medical diagnosis application on the cloud server network device with the one or more medical diagnosis methods with information from the first message, second message and third messages: (1) final diagnosis information including a final diagnosis for the one or more patient complaints for the specific patient at the medical facility, and (2) differential diagnosis information including one or more likely differential diagnoses and one or more critical differential diagnoses for the specific patient at the medical facility;

for creating automatically on the SaaS medical diagnosis application on the cloud server network device with the one or more diagnosis methods with information from the first message, second message and third messages: (1) an electronic visit summary for the specific patient at the medical facility supplied to the specific patient at the medical facility including the determined final diagnosis information and differential diagnosis information, (2) a new medical record for the specific patient at the medical facility including the determined final diagnosis information and differential diagnosis information, and (3) a treatment plan for the specific patient at the medical facility including the determined final diagnosis information and differential diagnosis information, the created electronic visit summary, the created new medical record and the created treatment plan reducing a second complexity level and a second risk level associated with determining a final diagnosis, one or more differential diagnoses created for the one or more patient complaints for the specific patient at the medical facility;

for determining automatically on the SaaS medical diagnosis application on cloud server network device a plurality of morbidity threat levels for the determined final diagnosis information, the determined differential diagnosis information including the one or more likely differential diagnoses and the determined one or more critical differential diagnoses for the specific patient at the medical facility, the determined plurality of morbidity threat levels reducing a third complexity level and a third risk level associated with diagnosing medical problems for the one or more patient complaints for the specific patient at the medical facility;

for storing from the SaaS medical diagnosis application on the cloud server network device the determined final diagnosis information and differential diagnosis information, the determined electronic visit summary, the created new medical record and the created treatment plan for the specific patient at the medical facility in the one or more cloud databases, including the one or more cloud storage objects comprising the one or more of the REpresentational State Transfer (REST), Simple Object Access Protocol (SOAP) or Lightweight Directory Access Protocol (LDAP) cloud storage objects, portions thereof, or combinations thereof, stored in the one or more cloud databases;

for displaying from the SaaS medical diagnosis application on the cloud server network device, diagnosis summary information related to the one on more patient complaints for the specific patient at medical facility on a third differential diagnosis display screen with a third plurality of sections on the GUI on the network device via the cloud communications network on the secure connection;

the diagnosis summary information including: final diagnosis information including: (1) the final diagnosis for the one or more patient complaints for the specific patient at the medical facility, (2) the differential diagnosis information including one or more likely differential diagnoses and critical differential diagnoses for the specific patient at the medical facility, (3) the created electronic visit summary for the specific patient at the medical facility supplied to the specific patient at the medical facility, (4) the created new medical record for the specific patient at the medical facility supplied to the specific patient at the medical facility (5) the created treatment plan for the specific patient; and for sending a fourth message from the from the SaaS medical diagnosis application on the cloud server network device to the network device via the cloud communications network on the secure connection, the fourth message including the created new medical record, the created electronic visit summary and the created treatment plan for the specific patient at the medical facility.

* * * * *